(12) United States Patent
Molard et al.

(10) Patent No.: US 11,618,829 B2
(45) Date of Patent: Apr. 4, 2023

(54) NANOCOMPOSITE MATERIAL MADE OF A POLYMER-MATRIX COMPRISING PEO-CONTAINING POLYMERS AND SALTS OF LUMINESCENT POLYANIONIC METAL CLUSTERS

(71) Applicants: Universite de Rennes 1, Rennes (FR); Centre National de la Recherche Scientifique (CNRS), Paris (FR); Universidade de Franca—UNIFRAN, Franca (BR)

(72) Inventors: Yann Molard, Acigne (FR); Maria De Los Angeles Amela-Cortes, Acigne (FR); Malo Robin, Lorient (FR); Stephane Cordier, Plelan le Petit (FR); Eduardo Ferreira Molina, Franca (BR)

(73) Assignees: Universite de Rennes 1, Rennes (FR); Centre National de la Recherche Scientifique (CNRS), Paris (FR); Universidade de Franca—UNIFRAN, Franca (BR)

( * ) Notice: Subject to any disclaimer, the term of this patent is extended or adjusted under 35 U.S.C. 154(b) by 433 days.

(21) Appl. No.: 16/759,804

(22) PCT Filed: Oct. 30, 2018

(86) PCT No.: PCT/EP2018/079748
§ 371 (c)(1),
(2) Date: Apr. 28, 2020

(87) PCT Pub. No.: WO2019/086477
PCT Pub. Date: May 9, 2019

(65) Prior Publication Data
US 2021/0179865 A1 Jun. 17, 2021

(30) Foreign Application Priority Data
Oct. 30, 2017 (EP) .................................. 17306490

(51) Int. Cl.
*C08K 3/11* (2018.01)
*C09D 5/22* (2006.01)
(Continued)

(52) U.S. Cl.
CPC .............. *C09D 5/22* (2013.01); *A01G 7/045* (2013.01); *C08J 9/0066* (2013.01); *C08J 9/283* (2013.01);
(Continued)

(58) Field of Classification Search
None
See application file for complete search history.

(56) References Cited

U.S. PATENT DOCUMENTS

2007/0023762 A1  2/2007  Gumins et al.

FOREIGN PATENT DOCUMENTS

KR    20150061740 A    6/2015
WO    WO-2015136306 A1 *  9/2015  ............ C07F 13/005

OTHER PUBLICATIONS

Cheplakova, Anastasia M., et al. "Nanosized mesoporous metal-organic framework MIL-101 as a nanocarrier for photoactive hexamolybdenum cluster compounds." Journal of Inorganic Biochemistry 166 (2017): 100-107. (Year: 2017).*

(Continued)

*Primary Examiner* — Robert S Loewe
(74) *Attorney, Agent, or Firm* — Banner & Witcoff, Ltd.

(57) ABSTRACT

The present invention concerns a solid nanocomposite material consisting of a polymer-matrix in which are dispersed alkali metal, hydronium or ammonium salts of polyanionic components, (Continued)

wherein the polymer-matrix comprises at least a linear or branched polymer or copolymer containing one or several poly(ethylene oxide) (PEO) chains, said polymer or copolymer being optionally crosslinked and each PEO chain having at least 4 ethylene oxide monomer units.

The present invention relates also to a photonic, e.g. optoelectronic, device comprising such a nanocomposite material.

Such material and device can be used as phosphorescence emitter, for crop growth lighting or for generating singlet oxygen.

23 Claims, 12 Drawing Sheets

(51) Int. Cl.
      A01G 7/04      (2006.01)
      C08J 9/00      (2006.01)
      C08J 9/28      (2006.01)
      C08K 5/00      (2006.01)
      C09D 183/12      (2006.01)
      C09K 11/68      (2006.01)
      A61N 5/06      (2006.01)
      H01L 33/50      (2010.01)

(52) U.S. Cl.
      CPC ............. *C08K 3/11* (2018.01); *C08K 5/0091* (2013.01); *C09D 183/12* (2013.01); *C09K 11/684* (2013.01); *A61N 5/062* (2013.01); *A61N 2005/0653* (2013.01); *C08J 2201/0502* (2013.01); *C08J 2383/12* (2013.01); *C08K 2201/011* (2013.01); *H01L 33/501* (2013.01)

(56) References Cited

OTHER PUBLICATIONS

Svezhentseva, Ekaterina V., et al. "Materials based on X-ray contrast octahedral metal cluster complexes and hydrophilic polymers." Materials Today: Proceedings 4.11 (2017): 11430-11436. (Year: 2017).*

Svezhentseva, Ekaterina V., et al. "Water-soluble hybrid materials based on {Mo 6 X 8} 4+(X=Cl, Br, I) cluster complexes and sodium polystyrene sulfonate." New Journal of Chemistry 41.4 (2017): 1670-1676. (Year: 2017).*

Elistratova, Julia, et al. "Supramolecular assemblies of triblock copolymers with hexanuclear molybdenum clusters for sensing antibiotics in aqueous solutions via energy transfer." RSC Advances 4.53 (2014): 27922-27930. (Year: 2014).*

Schubert "Polymers Reinforced by Covalently Bonded Inorganic Clusters" Chem. Mater. 2001, 13, 3487-3494.

Gross et al. Inorganic-organic Hybrid Materials from Poly (methylmethacrylate) Crosslinked by an Organically Modified Oxozirconium Cluster. Synthesis and Characterization. Polym. Adv. Tech. 2002, 13, 254-259.

Moraru et al. "Inorganic-Organic Hybrid Polymers by Polymerization of Methacrylate- or Acrylate-Substituted Oxotitanium Clusters with Methyl Methacrylate or Methacrylic Acid" Chem. Mater. 2002, 14, 2732-2740.

Qi et al. "Polyoxometalate/polymer hybridmaterials: fabrication and properties", Polym. Int. 2009, 58, 1217-1225.

Cotton "Metal Atom Clusters in Oxide Systems" Inorg. Chem. 1964, 3, 1217-1220.

Cordier et al. "Inorganic Molybdenum Octahedral Nanosized Cluster Units, Versatile Functional Building Block for Nanoarchitectonics" J. Inorg. Organomet. Polym. Mater. 2015, 25, 189-204.

Cordier et al. "Advances in the Engineering of Near Infrared Emitting Liquid Crystals and Copolymers, Extended Porous Frameworks, Theranostic Tools and Molecular Junctions Using Tailored Re6 Cluster Building Blocks" J. Cluster Sci. 2015, 26, 53-81.

Golden et al. "Monodisperse Metal Clusters 10 Angstroms in Diameter in a Polymeric Host: The "Monomer as Solvent" Approach" Science 1995, 268, 1463-1466.

Molard et al. "Red-NIR Luminescent Hybrid ACHTUNGTRENUNGPoly(methyl methacrylate) Containing Covalently Linked Octahedral Rhenium Metallic Clusters" Chem. Eur. J. 2010, 16, 5613-5619.

Molard et al. "Sensitization of Er3+ Infrared Photoluminiscence Embedded in a Hybrid Organic-Inorganic Copolymer containing Octahedral Molybdenum Clusters" Adv. Funct. Mater. 2013, 23, 4821-4825.

Amela-Cortes et al. Deep red luminescent hybrid copolymer materials with high transition metal cluster content J. Mater. Chem. C 2014, 2, 1545-1552.

Amela-Cortes et al. "Versatility of the ionic assembling method to design highly luminescent PMMA nanocomposites containing [M6Qi8La6]n? octahedral nano-building Blocks" Dalton Trans. 2016, 45, 237-245.

Molina et al. "Ureasil-polyether hybrid blend with tuneable hydrophilic/hydrophobic features based on U-PEO1900 and U-PPO400 mixtures" J. Sol-Gel Sci. Technol., 2014, 70:317-328.

Kirakci et al. "Synthesis and Characterization of Cs2Mo6X14 (X_ Br or I) Hexamolybdenum Cluster Halides: Efficient Mo6 Cluster Precursors for Solution Chemistry Syntheses" Z. Anorg. Allg. Chem., 2005, 631, 411.

Evans et al. "Controlling the Color Space Response of Colorimetric Luminescent Oxygen Sensors", Anal. Chem., 2006, 78, 5645.

Prévôt et al. "Electroswitchable red-NIR luminescence of ionic clustomesogen containing nematic liquid crystalline devices" J. Mater. Chem. C 2015, 3, 5152.

Prévôt et al. "Design and Integration in Electro-Optic Devices of Highly Efficient and Robust Red-NIR Phosphorescent Nematic Hybrid Liquid Crystals Containing [Mo 6 |8 (OCOC n F 2 n +1 ) 6 ] 2?( n=1, 2, 3) Nanoclusters" Adv. Funct. Mater. 2015, 25, 4966-4975.

Hummel et al. Characterization of Ax[W6I14] as Key Compounds for Ligand-Substituted A2[W6I8L6] Clusters Eur. J. Inorg. Chem. 2016, 5063-5067.

Lindner et al., "Uber die Chloride des zweiwertigen Molybdans, Wolframs und Tantals" Z. Anorg. Allg. Chem., 1923, 130, 209-228.

Sheldon et al. "Chloromolybdenum (II) Compounds" J. Chem. Soc., 1960, 1007-1014.

Schafer et al. Cli/ Br-Substitution in der Wolframchlorosaure (H3O)2[W6Cl8i]Cl6a 6H2O* Monatsh. Chem. 1971, 102, 1293-1304.

Jackson et al. "Oxygen Quenching of Electronically Excited Hexanuclear Molybdenum and Tungsten Halide Clusters" J. Phys. Chem., 1990, 94, 4500-4507.

Jackson et al. "Efficient Singlet Oxygen Generation from Polymers Derivatized with Hexanuclear Molybdenum Clusters" Chem. Mater., 1996, 8, 558-564.

Ghosh et al. "Fiber-optic oxygen sensor using molybdenum chloride cluster Luminescence" Appl. Phys. Lett., 1999, 75, 2885-2887.

Amela-Cortes et al. "Tuned red NIR phosphorescence of polyurethane hybrid composites embedding metallic nanoclusters for oxygen sensing" Chem. Commun., 2015, 51, 8177-8180.

Lu et al "Sub-nanometre sized metal clusters: from synthetic challenges to the unique property discoveries" Chemical Society Reviews, 2012, 41, 3594-3623.

Maverick et al. "Spectroscopic, Electrochemical, and Photochemical Properties of Molybdenum(II) and Tungsten(II) Halide Clusters" J. Am. Chem. Soc., 1983, 105, 1878-1882.

Robin et al. "Epoxy Based Ink as Versatile Material for Inkjet-Printed Devices" ACS Appl. Mater. Interfaces, 2015, 7, 21975-21984.

Sun et al. "Luminescent metal nanoclusters: controlled synthesis and functional applications", Science and Technology of Advanced Materials, 2014, 15, 014205.

(56) References Cited

OTHER PUBLICATIONS

Beltran et al. "A photobleaching resistant polymer supported hexanuclear molybdenum iodide cluster for photocatalytic oxygenations and photodynamic inactivation of Staphylococcus aureus" J. Mater. Chem. B, 2016, 4, 5975-5979.

Wang et al. "Enhanced photochromic efficiency of transparent and flexible nanocomposite films based on PEO-PPO-PEO and tungstate hybridization" J. Mater. Chem. C, 2015, 3, 177-186.

\* cited by examiner

● represents M, and
◯ represents $X^i$.

NANOCOMPOSITE MATERIAL MADE OF A POLYMER-MATRIX COMPRISING PEO-CONTAINING POLYMERS AND SALTS OF LUMINESCENT POLYANIONIC METAL CLUSTERS

RELATED APPLICATIONS

This application is a National Stage Application under 35 U.S.C. 371 of co-pending PCT application PCT/EP2018/079748 designating the United States and filed Oct. 30, 2018; which claims the benefit of EP application number 17306490.8 and filed Oct. 30, 2017 each of which are hereby incorporated by reference in their entireties.

The present invention relates to a polymer-matrix nanocomposite material embedded with alkali metal, hydronium or ammonium salts of polyanionic components, such as polyanionic metal clusters, and their applications as emissive materials.

In the present context of world overpopulation, scarcity of natural resources and climate change, the development of more efficient and environmentally friendly methods to grow plant products is of outmost importance.

Accordingly, the development of new light sources exhibiting improved performances with respect to plant growth is of particular relevance.

This has led to an ever-increasing interest for the use in light-emitting diodes (LEDs) in crop growth.

Two distinct light-mediated processes are involved in plants development, namely photosynthesis and photomorphogenesis.

Photosynthesis, which relies on light as a source of energy, needs high energy levels with large spectral bands to be absorbed notably by carotenoid and chlorophyll pigments. The Photosynthetically Active Radiation (PAR) spectrum, which corresponds to the wave band of solar radiation used by photosynthetic pigments, ranges from 400 to 700 nm.

In contrast, photomorphogenesis, which designates the response of plant growth patterns to light, necessitates low energy levels with narrow spectral bands. Various receptors are involved in the photomorphogenic effect of light, each type of which being sensitive to different portions of the electromagnetic spectrum. For instance, phytochromes are red-near infrared (NIR) light receptors that regulate the germination of seeds, the growth of seedlings, the synthesis of chlorophyll and the timing of blossoming.

However, a combination of numerous LEDs is necessary to target the PAR spectrum of plants, due to the fact that they emit actually in too narrow bands. Hence, this requires a more complicated electronic equipment to supply each LED with the suitable voltage. The development of a single LED able to achieve the intended purpose with respect to emissive properties is thus highly desirable.

Integration of emissive inorganic components in polymer matrices is particularly appealing to design easy to shape optoelectronic devices. Indeed, technologies such as dip coating, spin coating, drop casting or even printing can be used to deposit in a controlled manner such functional hybrid materials onto the desired substrate. Hence, it decreases largely the devices production costs compared to usual technics used to deposit inorganic components such as Chemical Vapor Deposition or Plasma induced Chemical Vapor Deposition.

Nonetheless, a particular focus should be made on the design of such materials to provide the best homogeneity possible in order to prevent phase segregation responsible of light scattering and premature ageing, while allowing a high inorganic doping content. To do so, the interactions between the organic and inorganic phases have to be carefully considered. Several strategies have been developed up to now, beside the simple physical blending technic that leads to phase segregation with ageing, given that the interactions between the organic and inorganic components are not strong enough to maintain the assembling in a homogeneous way. The most obvious approach is the covalent grafting of organic monomers moieties on the inorganic emitter followed by a copolymerization process [a) Schubert, *Chem. Mater.* 2001, 13, 3487-3494; b) Gross et al., *Polym. Adv. Tech.* 2002, 13, 254-259; c) Moraru et al., *Chem. Mater.* 2002, 14, 2732-2740.]. The second strategy relies on electrostatic interactions between the polymerizable entities and the inorganic moieties, and was used by e.g. L. Wu et al. to integrate polyoxometalate polyanions in acrylate matrices [Qi, Wu, *Polym. Int.* 2009, 58, 1217-1225.].

With respect to emissive inorganic components, octahedral clusters based on a Mo, W or Re scaffold, which can be considered as intermediates between transition metal complexes and nanoparticles [Cotton, *Inorg. Chem.* 1964, 3, 1217-1220], are of tremendous interest They are obtained as ternary salt ceramic like powders of general formula $A_nM_6X^i{}_8L^a{}_6$ (with A=Cs or K; M=Mo, W or Re, and $X^i$ and $L^a$ representing respectively inner and apical ligands) by high temperature synthesis, and emit very efficiently in the red and near infrared (red-NIR) area when excited in the UV-blue region (internal quantum efficiency up to 100% have been reported). Several groups developed in the past few years strategies to integrate these phosphorescent emitters in hybrid materials [a) Cordier et al., *J. Inog. Organomet. Polym. Mater.* 2015, 25, 189-204; b) Cordier et al., *J. Cluster Sci.* 2015, 26, 53-81]. In all cases, a modification of the ternary salt was necessary to maximize the interactions between components, either by a covalent grafting of polymerizable organic units on the clusters apical positions or by a metathesis reaction involving the exchange of the alkali cations with a polymerizable organic cation [respectively a) Golden et al., *Science* 1995, 268, 1463-1466; b) Molard et al., *Chem. Eur. J.* 2010, 16, 5613-5619; c) Molard et al., *Adv. Funct. Mater.* 2013, 23, 4821-4825; and d) Amela-Cortes et al., *J. Mater. Chem. C* 2014, 2, 1545-1552; e) Amela-Cortes et al., *Daton Trans.* 2016, 45, 237-245].

There exists thus a need for a new way of introducing emissive ternary salts in a host matrix, in which the emissive ternary salt is integrated without any chemical modifications, keeping thus intact its intrinsic properties.

The inventors of the present invention have thus developed a new strategy for preparing such functional hybrid materials relying on weak interactions between poly(ethylene oxide) (PEO) chains and the alkali metal, hydronium or ammonium ions that counterpart the polyanionic charge of a polyanionic component such as a polyanionic metal cluster.

The resulting nanocomposite materials combine the ease of processing of organic polymer inks with the strong red-NIR phosphorescence of the inorganic emitter (metal cluster), thus paving the way for various optoelectronic applications, including in the field of plant growth.

Besides, said nanocomposite materials have proved to be permeable to gases, which opens up promising perspectives for these materials as gas sensors, notably as oxygen sensors.

Moreover, the inventors of the present invention have demonstrated that quite surprisingly, a simple device consisting of a commercial blue LED coated with a film based on a nanocomposite material according to the invention can act as a local singlet oxygen generator, and therefore could find applications in photodynamic therapy or in the development of bactericidal coating.

The present invention thus relates to a solid nanocomposite material consisting of a polymer-matrix in which are dispersed alkali metal, hydronium or ammonium salts of polyanionic components,
wherein the polymer-matrix comprises at least a linear or branched polymer or copolymer containing one or several poly(ethylene oxide) (PEO) chains, said polymer or copolymer being optionally crosslinked and each PEO chain having at least 4 ethylene oxide monomer units.

In particular, the present invention relates to a solid nanocomposite material consisting of a polymer-matrix in which are dispersed alkali metal, hydronium or ammonium salts, notably alkali metal salts of polyanionic metal clusters, wherein the polymer-matrix comprises at least a linear or branched polymer or copolymer containing one or several poly(ethylene oxide) (PEO) chains, said polymer or copolymer being optionally crosslinked and each PEO chain having at least 4 ethylene oxide monomer units, and wherein the salts of polyanionic metal clusters interact with the polymer-matrix solely by means of weak interactions in between the alkali metal, hydronium or ammonium cations and the PEO chains of polymer or copolymer.

In the context of the present invention, the expression "solely by means of weak interactions" means that the salts of the polyanionic metal clusters are not covalently bound to the polymer-matrix.

Nanocomposite Material

Within the meaning of this invention, "a nanocomposite material" is intended to designate a material resulting from the combination of a bulk matrix and nano-dimensional phase(s) embedded in said bulk matrix. By "nano-dimensional phase" is understood a phase having one, two or three dimensions of less than 100 nanometers (nm).

In the present invention, it is a polymer-matrix nanocomposite material, namely a polymer matrix in which are dispersed nanoparticles. By "nanoparticle" is understood a particle between 1 and 100 nm in size. In the present invention, the nanoparticles are the metal clusters.

The nanocomposite material according to the present invention is thus a solid material.

The PEO chains each comprising at least 4 ethylene oxide monomer units interact by means of weak interaction with the alkali metal cation, hydronium or ammonium ion, as illustrated notably on FIG. 6b, so as to homogeneously incorporate the alkali metal, hydronium or ammonium salts of polyanionic components in the polymer-matrix, without phase segregation.

Advantageously, the alkali metal, hydronium or ammonium salts of polyanionic components represent 0.01 wt % to 80 wt %, in particular 0.01 wt % to 50 wt %, notably 0.01 wt % to 10 wt % of the total weight of the nanocomposite material.

Advantageously, the polymer-matrix represents 20 wt % to 99.99 wt %, in particular 50 wt % to 99.99 wt %, notably 90 wt % to 99.99 wt % of the total weight of the nanocomposite material.

Salts of Polyanionic Components

In the present invention, the polyanionic components can be present in the nanocomposite in the form of alkali metal, hydronium or ammonium salts, notably alkali metal salts.

"Alkali metal" as used in the present invention refers to lithium (Li), sodium (Na), potassium (K), rubidium (Rb), caesium (Cs) or francium (Fr), preferably Cs, Na or K, more preferably Cs or K.

"Ammonium" as used in the present invention refers to a $NR_1R_2R_3R_4^+$ cation, where $R_1$-$R_4$ represent, independently of each other, a hydrogen atom or a $C_1$-$C_6$ alkyl group, notably a hydrogen atom or a $C_1$-$C_3$ alkyl group, preferably a hydrogen atom.

"Hydronium" as used in the present invention refers to the $H_3O^+$ ion.

A "$C_1$-$C_6$ alkyl", respectively "$C_1$-$C_3$ alkyl", group means a linear or branched saturated hydrocarbon chain comprising 1 to 6, respectively 1 to 3, carbon atoms. it can be for example a methyl or ethyl group.

The polyanionic component has advantageously 2 to 5 negative charge, notably 2.

The polyanionic component can be a polyanionic metal cluster, having in particular luminescent properties.

Luminescence is emission of light by a substance not resulting from heat; this distinguishes luminescence from incandescence, which is light emitted by a substance as a result of heating. It is, thus, a form of cold body radiation. The energy of the electrons shifts upon excitation before going back to its base level. When the electrons return to their base level of energy, light is emitted. Fluorescence is luminescence wherein light emission occurs right after excitation, usually $10^{-9}$ to $10^{-6}$ s after the excitation. Phosphorescence is luminescence wherein light emission occurs after a longer lapse of time from the excitation, usually $10^{-6}$ to 10 s.

Definition of a metal cluster is given by F. A. Cotton in *Inorg. Chem.* 1964, 3, 1217 as: "a finite group of metal atoms that are held together mainly, or at least to a significant extent, by bonds directly between the metal atoms, even though some non-metal atoms may also be intimately associated with the cluster".

In the following description, "metal cluster" is understood as at least two metal atoms which are covalently bound together and form metal-metal bonds. Metal-metal bonds enable delocalisation of all valence electrons on all metal atoms. The metal atoms of the metal cluster form a polyhedron. Each metal atom is considered as occupying a vertex (corner point) of the polyhedron.

The "metal cluster" may comprise at least face-capping ligands and/or edge bridging ligands, together referred as inner ligands.

A "ligand" is an ion or molecule that binds to the metal cluster to form a coordination complex. The bonding between the metal cluster and the ligand usually involves formal donation of one or more of the ligand's electron pairs.

"Face-capping ligands" are ligands that are located normally to the centre of one face of the polyhedron, i.e. the virtual line passing through the ligand and the centre of the face of the polyhedron is orthogonal to that very face.

"Edge-bridging ligands" are ligands that are located normally to the middle of a metal-metal bond, i.e. the virtual line passing through the ligand and the middle of the metal-metal bond is perpendicular to that very metal-metal bond.

The metal cluster can comprise apical ligands.

"Apical ligands" are ligands located facing the vertexes of the polyhedron. The metal cluster and the inner ligands are referred together in the description as a "cluster core". The cluster core and the apical ligands are referred together as a "cluster unit".

The term "metal cluster" as used in the present invention refers to a metal cluster as defined above having a nanometric size, preferably between about 0.5 nm to about 20 nm, more preferably between about 0.5 nm to about 2 nm and bearing at least two negative charges, such as 2 to 5, notably 2.

The polyanionic metal clusters are advantageously octahedral.

In a particular embodiment of the present invention, the alkali metal, hydronium or ammonium salts of the polyanionic metal clusters are salts or a mixture of salts of the general formula $A_nM_6X^i{}_8L^a{}_6$, wherein:

A represents caesium (Cs), potassium (K), sodium (Na), a hydronium, an ammonium or a mixture thereof;

n corresponds to the number of negative charges of the polyanionic metal cluster ($[M_6X^i{}_8L^a{}_6]^{n-}$) and ranges from 2 to 5;

M represents molybdenum (Mo), rhenium (Re), tungsten (W) or a mixture thereof;

$X^i$ is an inner ligand and represents a halogen, a chalcogen atom, or a mixture thereof; and $L^a$ is an apical ligand and represents a halogen atom, an organic ligand or a mixture thereof.

The term "halogen" as used in the present invention refers to an atom of fluorine (F), chlorine (Cl), bromine (Br), iodine (I), astatine (At) or tennessine (Ts), preferably F, Cl, Br or I.

The term "chalcogen" as used in the present invention refers to an atom of oxygen (O), sulphur (S), selenium (Se), tellurium (Te), polonium (Po) or livermorium (Lv), preferably O, S, Se or Te.

The term "organic ligand" as used in the present invention refers to an ion or a molecule that binds to a metal atom via a carbon, oxygen, nitrogen, sulphur or phosphorus atom. It can be notably CN, a carboxylate, SCN, $NO_3$, $NO_2$, $C_5H_5N$, $NH_3$, $NH_2$—$(CH_2)_2$—$NH_2$, $NCH_4$—$CH_4N$, $P(C_6H_5)_3$, O=$P(C_6H_5)_3$ or CO, particularly SCN, CN or a carboxylate, more particularly SCN or a carboxylate.

"Carboxylate" means, in the present invention, a group $R_5$—COO where $R_5$ represents a $C_1$-$C_{17}$ alkyl group, notably a $C_1$-$C_6$ alkyl group, notably a $C_1$-$C_3$ alkyl group, in which one or several hydrogen atoms each can be replaced by a fluorine atom. It can be in particular a perfluorinated $C_1$-$C_{17}$ alkyl group, notably a perfluorinated $C_1$-$C_6$ alkyl group, notably a perfluorinated $C_1$-$C_3$ alkyl group, i.e. a $C_1$-$C_3$ alkyl group in which all the hydrogen atoms have been replaced with a fluorine atom, such as a $C_2F_5COO$ or a $C_3F_7COO$ group.

A "$C_1$-$C_{17}$ alkyl" group means a linear or branched saturated hydrocarbon chain comprising 1 to 17 carbon atoms.

In this particular embodiment, each polyanionic metal cluster is thus of the general formula $[M_6X^i{}_8L^a{}_6]^{n-}$, wherein n, M, $X^i$ and $L^a$ are as defined above.

Such a polyanionic metal cluster comprises a metal cluster with six metal atoms M, 8 face-capping ligands $X^i$ and six apical ligands $L^a$, and corresponds to the structure represented on FIG. 15.

M represents Mo, Re, W or a mixture thereof, preferably Mo or W.

$X^i$ represents a halogen, a chalcogen atom, or a mixture thereof.

Among the halogens, F, Cl, Br, I and a mixture thereof are preferred. The most preferred halogens are Cl, Br, I and a mixture thereof.

Among the chalcogens, O, S, Se, Te or a mixture thereof are preferred. The most preferred chalcogen is Se.

Advantageously, $X^i$ is Cl, Br or I.

$L^a$ represents a halogen atom, an organic ligand or a mixture thereof.

Among the halogens, F, Cl, Br, I and a mixture thereof are preferred. The most preferred halogens are Cl, Br, I and a mixture thereof.

Among the organic ligand, SCN, CN, carboxylates and a mixture thereof are preferred. The most preferred organic ligands are SCN and carboxylates such as a $C_2F_5COO$ or a $C_3F_7COO$ group.

Advantageously, $L^a$ is C, Br, I, CN, SCN or a carboxylate, notably Cl, Br, I, SCN or a carboxylate, in particular Cl, I, Br, SCN, a $C_2F_5COO$ or a $C_3F_7COO$ group.

In particular, each polyanionic metal cluster is of the general formula $[M_6X^i{}_6L^a{}_6]^{n-}$, wherein:

n is equal to 2;

M represents Mo or W;

$X^i$ represents Cl, Br, I, or a mixture thereof; and $L^a$ represents Cl, Br, I, CN, SCN, a carboxylate or a mixture thereof.

Advantageously, each polyanionic metal cluster is of the general formula $[M_6X^i{}_8L^a{}_6]^{n-}$, wherein:

n is equal to 2;

M represents Mo or W;

$X^i$ represents Cl, Br or I; and $L^a$ represents Cl, I, Br, SCN, a $C_2F_5COO$ or a $C_3F_7COO$ group.

The alkali metal salt is preferably a potassium or caesium salt, more preferably a caesium salt.

The ammonium salt is preferably a $NH_4^+$ salt.

In a particular embodiment, the alkali metal, hydronium or ammonium salt of the metal cluster anion is of the general formula $A_nM_6X^i{}_6L^a{}_6$, wherein A represents a hydronium or an ammonium, Na, K or Cs, preferably Cs, K, $H_3O$ or $NH_4$, more preferably Cs and n, M, $X^i$ and $L^a$ are as defined above.

In a preferred embodiment, the alkali metal, hydronium or ammonium salts of the polyanionic metal clusters are salts or a mixture of salts of the general formula $A_nM_6X^i{}_6L^a{}_6$, wherein:

A represents $H_3O$, $NH_4$, Cs, Na or K, preferably $H_3O$, $NH_4$, Cs or K;

n is equal to 2;

M represents Mo or W;

$X^i$ represents Cl, Br, I, or a mixture thereof; and $L^a$ represents C, Br, I, SCN, CN, a carboxylate such as $C_3F_7COO$ or a $C_2F_5COO$ group, or a mixture thereof.

In a most preferred embodiment, the alkali metal salts of the polyanionic metal clusters are salts or a mixture of salts of the general formula $A_nM_6X^i{}_6L^a{}_6$, wherein:

A represents Cs;

n is equal to 2;

M represents Mo or W;

$X^i$ represents Cl, Br or 1; and $L^a$ represents C, Br, I, SCN, a $C_3F_7COO$ or a $C_2F_5COO$ group.

In particular, the alkali metal, hydronium or ammonium salts of the polyanionic metal clusters are selected from the group consisting of $Cs_2Mo_6Br_{14}$, $Cs_2Mo_6Cl_{14}$, $Cs_2Mo_6I_{14}$, $Cs_2Mo_6Br_8Cl_6$, $Cs_2Mo_6Br_6I_6$, $Cs_2Mo_6I_8(OCOC_2F_5)_6$, $Cs_2Mo_6I_8(OCOC_3F_7)_6$, $Cs_2W_6I_{14}$, $K_2Mo_6Cl_{14}$, $(H_3O)_2Mo_6Cl_{14}$, $(H_3O)_2W_6Cl_{14}$, $(NH_4)_2Mo_6Br_8SCN_6$ and mixtures thereof, preferably said alkali metal, hydronium or ammonium salts of the luminescent polyanionic metal clusters are $Cs_2Mo_6Br_{14}$, $Cs_2W_6I_{14}$, $(NH_4)_2Mo_6Br_8SCN_6$, $(H_3O)_2Mo_6Cl_{14}$ and/or $Cs_2Mo_6I_6(OCOC_2F_5)_6$.

Polymer-Matrix

The polymer-matrix according to the invention comprises at least a linear or branched polymer or copolymer containing one or several poly(ethylene oxide) (PEO) chains, said polymer or copolymer being optionally crosslinked and each PEO chain having at least 4 ethylene oxide monomer units.

Thus, the polymer or copolymer according to the present invention is either a linear PEO polymer or a linear or branched copolymer containing one or several poly(ethylene oxide) (PEO) chains. When the copolymer is branched, the said PEO chains can be present on the backbone (i.e. main chain/longer chain) of the branched copolymer and/or as side-chains grafted onto the backbone chain of the branched copolymer.

The polymer or copolymer contains at least 4, notably between 4 and 200 ethylene oxide (EO) monomer units.

Beside the one or several poly(ethylene oxide) (PEO) chains, the copolymer may include one or several polymer chains chosen from the group consisting of polyamide, polycarbonate, polyethylene (PE), polyethylene naphthalate (PEN), polyethylene terephthalate (PET), polyimide, polymethylmethacrylate (PMMA), polystyrene (PS), polyurethane, polycarbamate, polyester, polydimethylsiloxane (PDMS), polyacrylic acid (PA), polyurethane (PU) polyvinylpyrrolidone (PVP), polyacrylamide (PAM), alkyde, polycaprolactone and a mixture thereof.

The polymer or copolymer also can comprise crosslinkable monomer units so as to be crosslinked. Said crosslinkable monomer units can be a ureasil or urethanesil group.

The polymer or copolymer can comprise also one or several light-emitting moieties grafted on said polymer or copolymer. Said light-emitting moieties can be for example a crosslinked ureasil or urethanesil group.

A ureasil or urethanesil group according to the invention is a group comprising a urea or urethane moiety and a siloxane moiety. It can have the following formula:

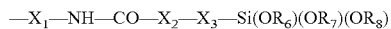

wherein:
- $X_1$ is a bond or a divalent linear or branched saturated hydrocarbon group having advantageous 1 to 6, notably 1 to 3 carbon atoms, such as —CH$_2$—CH(Me)-,
- $X_2$ is NH (for ureasil group) or O (for urethanesil group),
- $X_3$ is a divalent linear or branched saturated hydrocarbon group having advantageous 1 to 6, notably 1 to 3 carbon atoms, preferably —(CH$_2$)$_p$ with p comprised between 1 and 6, notably comprised between 1 and 3,
- $R_6$, $R_7$ and $R_8$ are, independently of one another, (C$_1$-C$_6$) alkyl, preferably (C$_1$-C$_3$)alkyl, such as methyl or ethyl.

The crosslinked ureasil or urethanesil group is obtained after hydrolysis of the siloxane group (—Si(OR$_6$)(OR$_7$)(OR$_6$) leading to —Si(OR$_6$)(OR$_7$)(OH)) and condensation of the obtained silanol groups.

According to a particular embodiment, the polymer-matrix comprises, notably consists in, a linear PEO polymer, optionally with one or two light-emitting moieties, such as defined above, grafted on its extremities, such a PEO polymer being advantageously crosslinked with said light-emitting moieties. Advantageously the PEO polymer contains at least 4, notably between 9 and 100 ethylene oxide (EO) monomers.

According to another particular embodiment, the polymer-matrix comprises, notably consists in, a branched copolymer containing PEO chains grafted as side-chains onto the backbone chain of the copolymer. Each side-chains contain at least 4, notably between 6 and 120 ethylene oxide (EO) monomers. Advantageously, the total amount of ethylene oxide (EO) monomers in the copolymer is at least 0.1 wt %, notably between 0.5 wt % and 10 wt % of the total weight of the copolymer.

According to still another particular embodiment, the polymer-matrix comprises, notably consists in, a linear or branched copolymer containing one or several poly(ethylene oxide) (PEO) chains that are part of the backbone chain of the copolymer. Advantageously the copolymer contains at least 4, notably between 6 and 200 ethylene oxide (EO) monomers.

According to a particular embodiment, the polymer or copolymer is selected from the group consisting of PEO, crosslinked PEO-ureasil, crosslinked PEO-urethanesil polymethylmethacrylate-poly(ethylene oxide) methacrylate (PMMA-PEOMA), PDMS-PEO, PVP-PEO, PU-PEO, PS-PEO, Polyethylene-PEO, polyester-PEO, polyamide-PEO, polycaprolactone-PEO and mixtures thereof.

Manufacturing Method

The nanocomposite material according to the present invention can be prepared according to various methods.

The present invention relates thus to a first process for preparing a nanocomposite material according to the present invention comprising a step of dipping the polymer-matrix in a solution containing the dissolved alkali metal, hydronium or ammonium salts of the polyanionic components.

Such a dipping step allows the alkali metal, hydronium or ammonium salts of the polyanionic components to adsorb in the polymer-matrix.

The concentration of the alkali metal, hydronium or ammonium salts of the polyanionic components will depend on the amount of salts to be adsorbed in the polymer-matrix. For example, this concentration can be comprised between 0.05 mg/mL and 100 mg/mL, notably between 1 mg/mL and 10 mg/mL.

The duration of the dipping step will depend notably on the concentration of the alkali metal, hydronium or ammonium salts of the polyanionic components. For example, this duration can be comprised between 10 minutes and 48 h, notably between 10 h and 30 h.

The solvent of the solution can be any solvent or mixture of solvents able to solubilize the alkali metal, hydronium or ammonium salts of the polyanionic components but not the polymer-matrix which is in a solid state. This solvent can be water, an alcohol such as ethanol, acetone, acetonitrile (CH$_3$CN), THF (tetrahydrofuran), DMF (dimethylformamide), DMSO (dimethyl sulfoxide), ethyl acetate, chloroform, dichloromethane or a mixture thereof.

The present invention relates also to a second process for preparing a nanocomposite material according to the invention comprising a step:
- of polymerizing the monomer units of the polymer or copolymer according to the invention or
- of crosslinking a polymer or copolymer precursor in order to obtained a crosslinked polymer or copolymer according to the invention, in a reaction medium containing the alkali metal, hydronium or ammonium salts of the polyanionic metal clusters.

The concentration of the alkali metal, hydronium or ammonium salts of the polyanionic components in the reaction medium will depend on the amount of salts to be adsorbed in the polymer-matrix. For example, this concentration can be comprised between 0.05 wt % and 20 wt %.

The polymerizing and crosslinking steps can be performed in common conditions well-known to the one skilled in the art.

Photonic Device

The present invention is also directed to a photonic device comprising a nanocomposite material according to the present invention.

A photonic device as used in the present invention is a device for creating, manipulating or detecting light, preferably creating light. It can be in particular an optoelectronic device, i.e. an electronic device that operates on both light and electrical currents. This can be in particular an electrically driven light source such as a light-emitting diode (LED).

In particular, the photonic device according to the present invention can be alight-emitting diode (LED) coated with a film of a nanocomposite material according to the present invention.

The film of nanocomposite material can be deposited on the LED by any method known to the one-skilled in the art to apply a polymer layer on a substrate. For example, the film can be applied by inkjet printing or by spraying a solution of the nanocomposite material. Any solvent able to solubilize the nanocomposite material can be used.

Applications

As indicated previously, the nanocomposite material according to the invention has various properties and thus applications.

The present invention relates thus to the use of a nanocomposite material or a photonic device according to the invention as a phosphorescence emitter, preferably in the red-near infrared (red-NIR) region of the electromagnetic spectrum, which ranges from 600 nm to 950 nm.

This phosphorescence is due to the presence of the polyanionic component, preferably a polyanionic metal cluster, such as a metal cluster of general formula $[M_6X^i_8L^a_6]^{n-}$ described above. The phosphorescence will be obtained notably after absorption of light having a wavelength in the range comprised between 340 nm and 480 nm.

Such a property can be used for crop growth lighting as explaining previously. A LED coated with a nanocomposite material according to the invention will be particularly useful as light source for crop growth.

The present invention relates also to the use of a nanocomposite material or a photonic device according to the invention for generating singlet oxygen as illustrated in example 2.

The singlet oxygen can be used in photodynamic therapy for treating a melanoma or for a bactericidal treatment.

FIGURES

Figure 4:
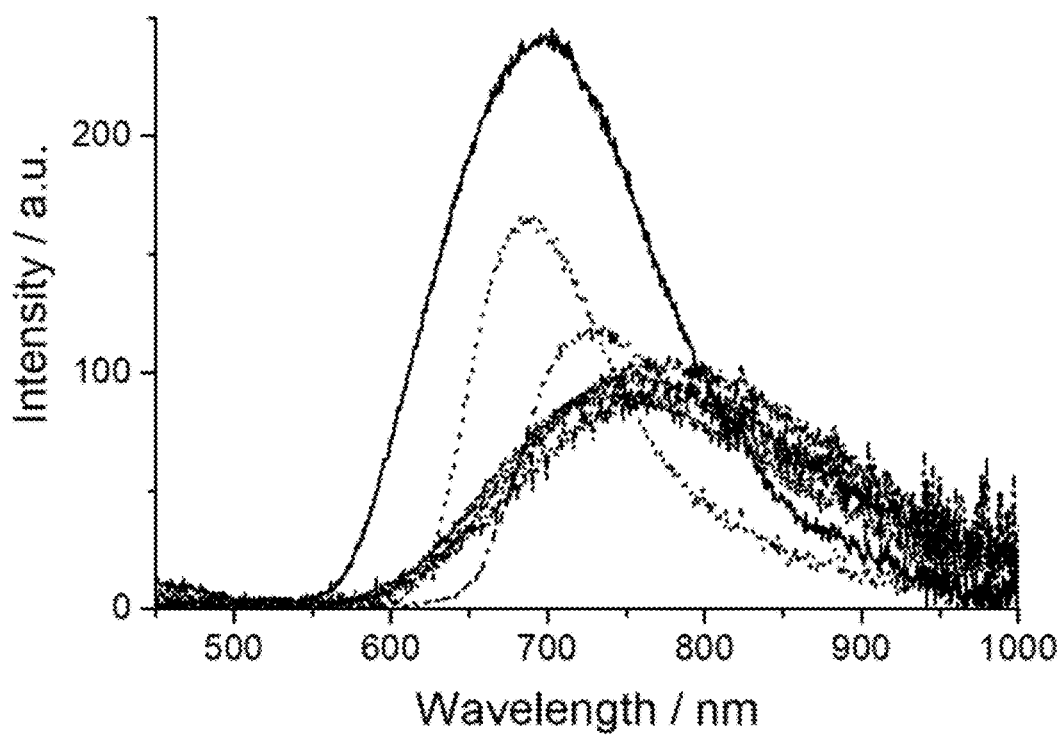

FIG. 4 displays the emission spectra of PEO1900 samples doped at 10 wt % with $Cs_2W_6I_{14}$ (plain line), $Cs_2Mo_6I_{14}$ (dashed line), $Cs_2Mo_6I_8(OCOC_3F_7)_6$ (dotted line), $Cs_2Mo_6Cl_{14}$ (dashed-dotted line), $Cs_2Mo_6Br_{14}$ (dashed-dotted-dotted line) $Cs_2Mo_6Br_8I_6$ (short-dashed line) or $Cs_2Mo_6Br_8Cl_6$ (short-dotted line).

Figure 5:
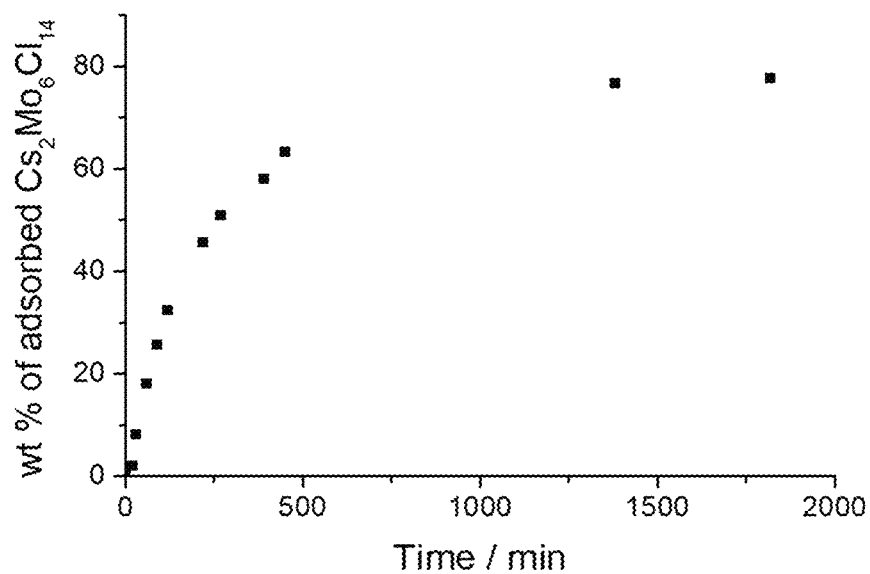

FIG. 5 represents adsorption kinetic studies of $Cs_2Mo_6Cl_{14}$ (starting concentration 10 mg·mL$^{-1}$) by PEO1900 matrix.

Figure 6A:
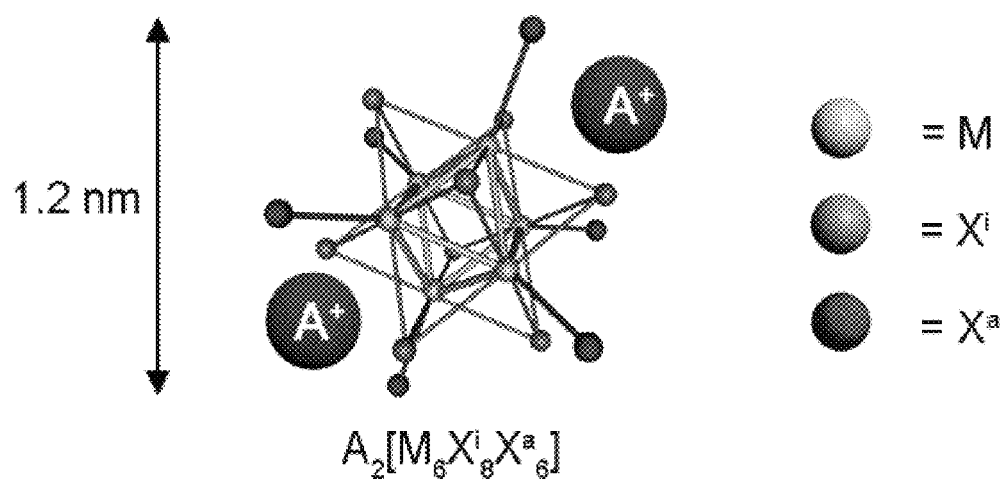

FIG. 6a corresponds to a schematic representation of a ternary cluster salt of general formula $A_2[M_6X^i_8X^a_6]$.

Figure 6B:
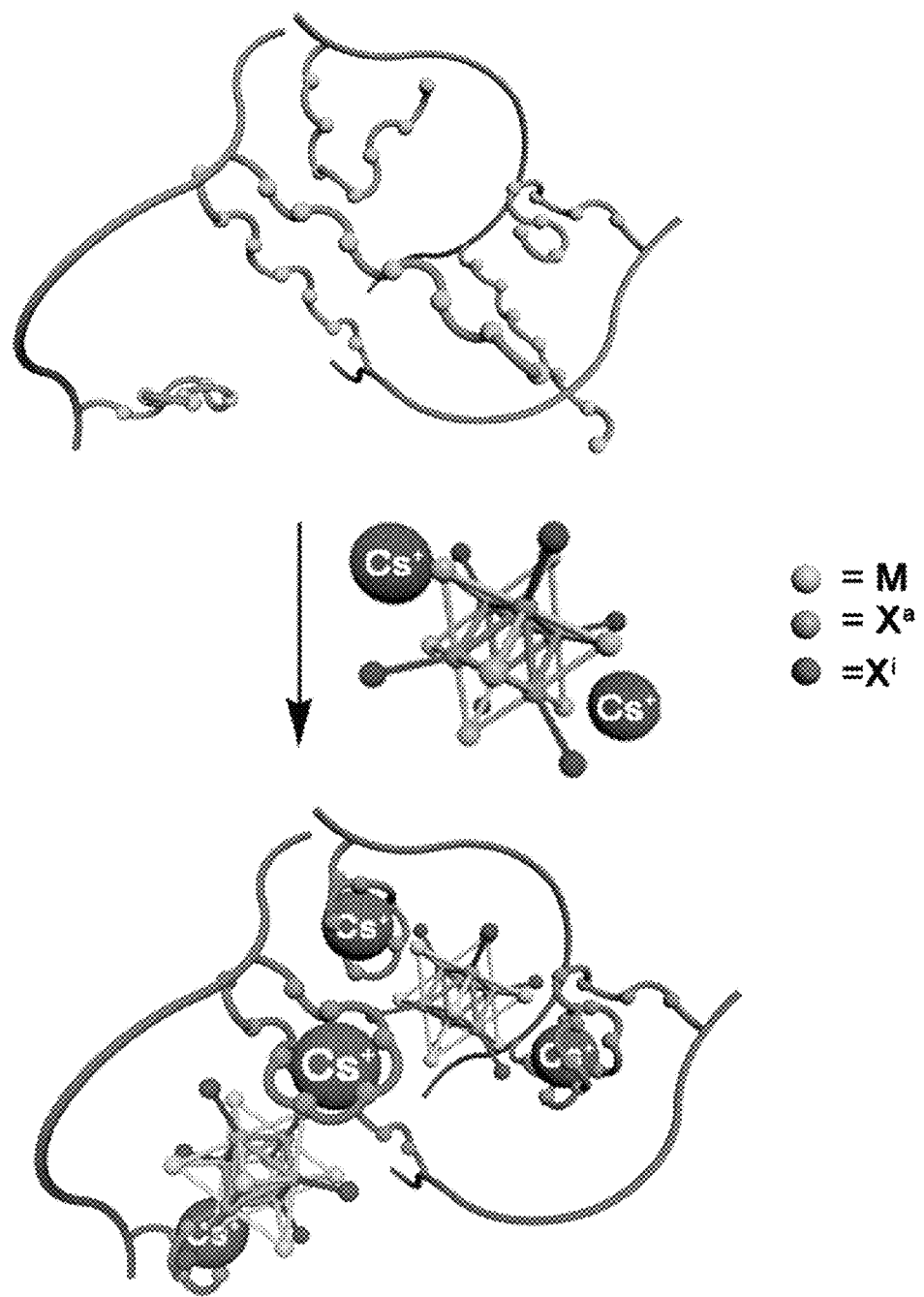

FIG. 6b corresponds to a schematic representation of the integration of the cluster ternary salt $Cs_2[M_6X^i_8X^a_6]$ in the polymer-matrix.

Figure 7:
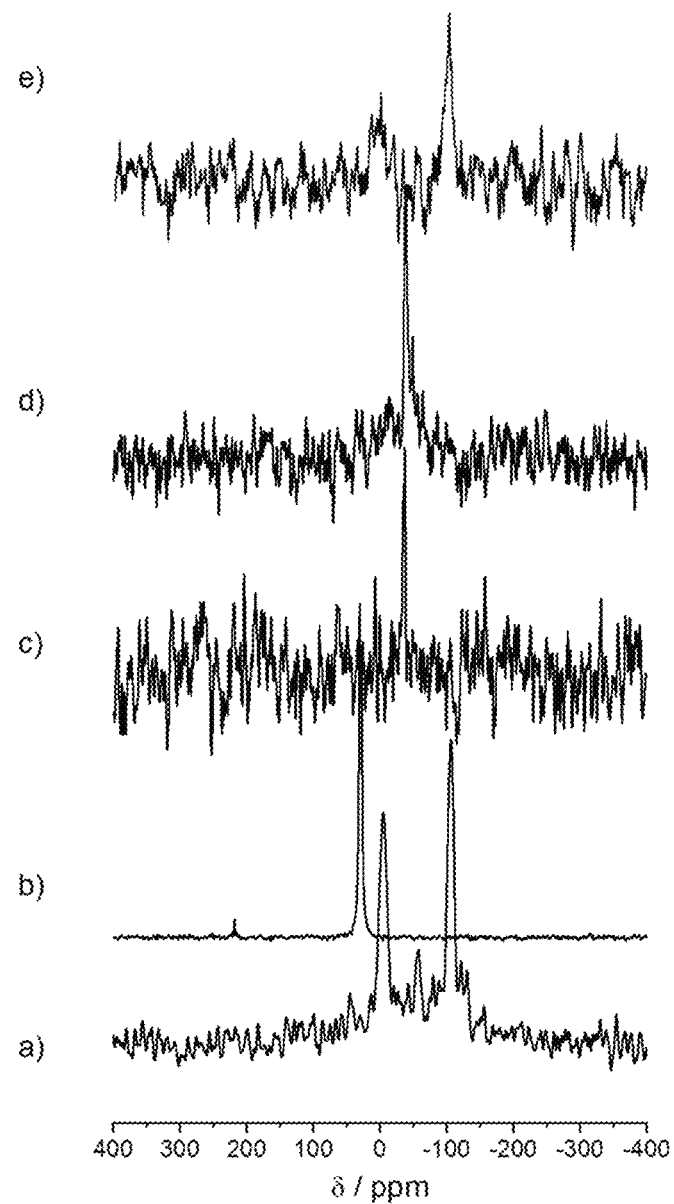

FIG. 7 represents $^{133}Cs$ MAS NMR spectra of a) crystalline $Cs_2Mo_6I_8(OCOC_2F_5)_6$, b) $P_1C$, c) $P_2C$, d) $P_5C$ and e) mixture of $Cs_2Mo_6I_8(OCOC_2F_5)_6$ with pure PMMA.

Figure 8:
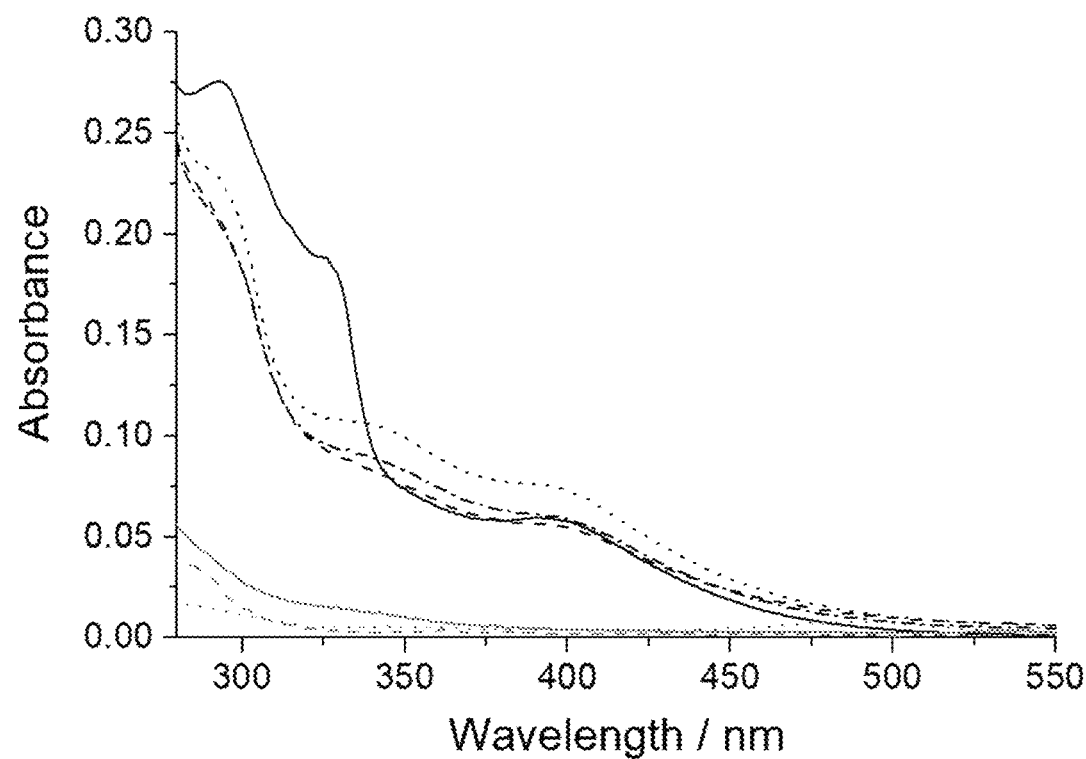

FIG. 8 represents absorption spectra of $CH_3CN$ solutions containing $Cs_2Mo_6I_8(OCOC_2F_5)_6$ (black plain line), doped $P_1C$ (black dashed line), doped $P_2C$ (black dotted line), doped $P_5C$ (black dash-dotted line), pure $P_1$ (grey dotted line), pure P2 (grey dashed line) and pure P5 (grey plain line).

Figure 9:
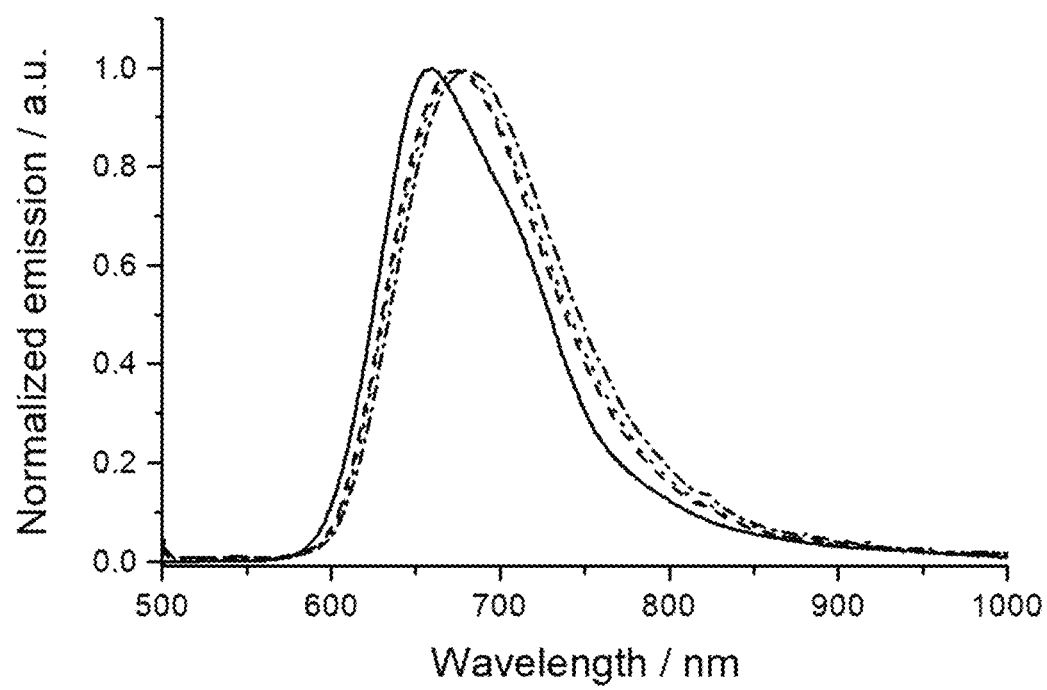

FIG. 9 represents normalized emission spectra at $\lambda_{exc}$=370 nm of $Cs_2Mo_6I_8(C_2F_5OCO)_6$ (plain line), doped $P_1C$ (dashed line), doped $P_2C$ (dotted line) and $P_5C$ (dash-dotted line).

Figure 10A:
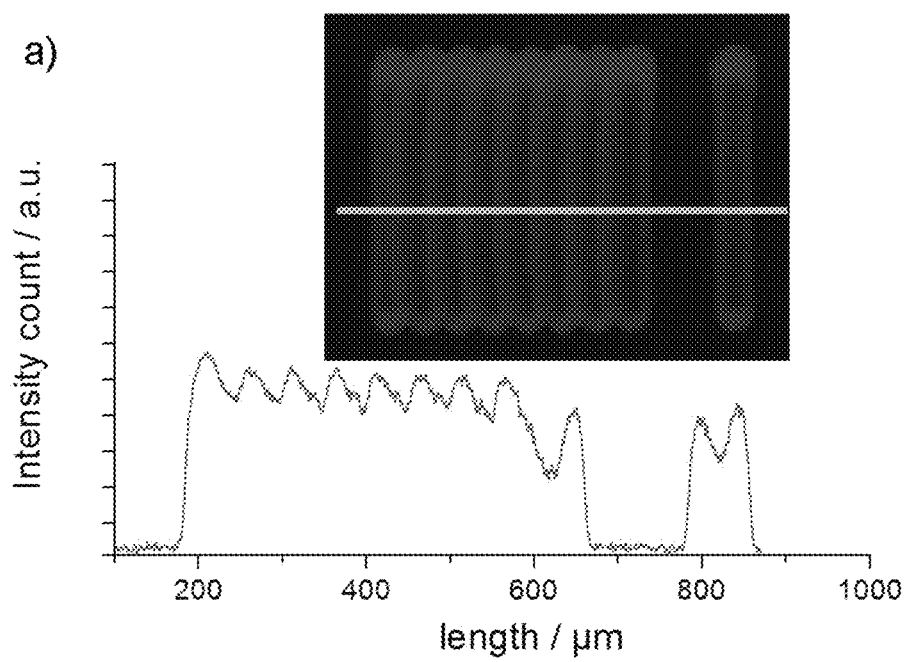
Figure 10B:
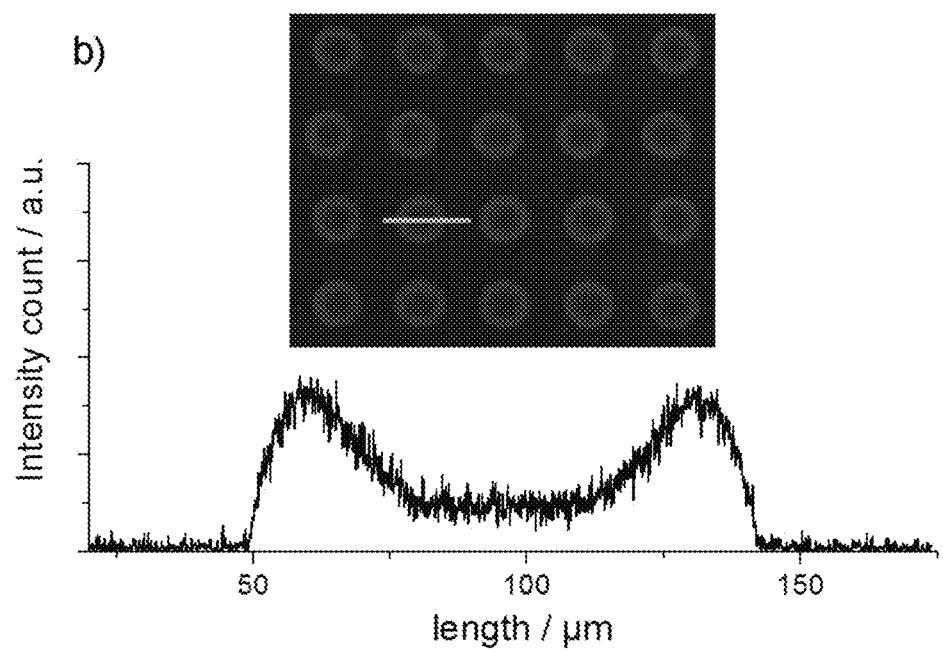

FIGS. 10a and 10b represent InkJet printed $P_1C$ patterns under UV light excitation and corresponding colorimetric profiles for a) thin films and b) drops.

Figure 11A:
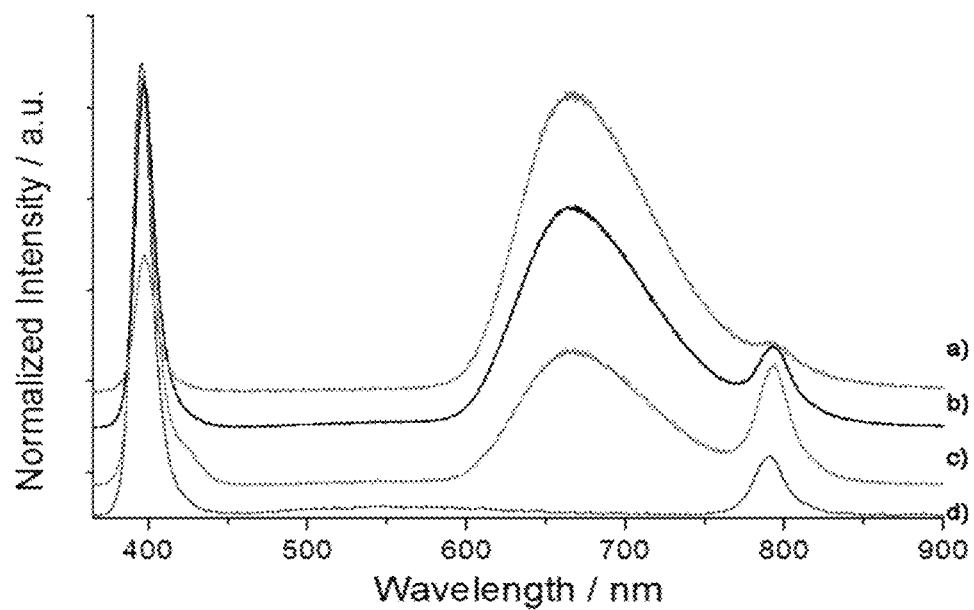

FIG. 11a represents emission spectra recorded for 395 nm commercial blue LED (d) and $P_1C$ covered blue LED recorded at 0° (c), 30° (b) and 60° (a).

Figure 11B:
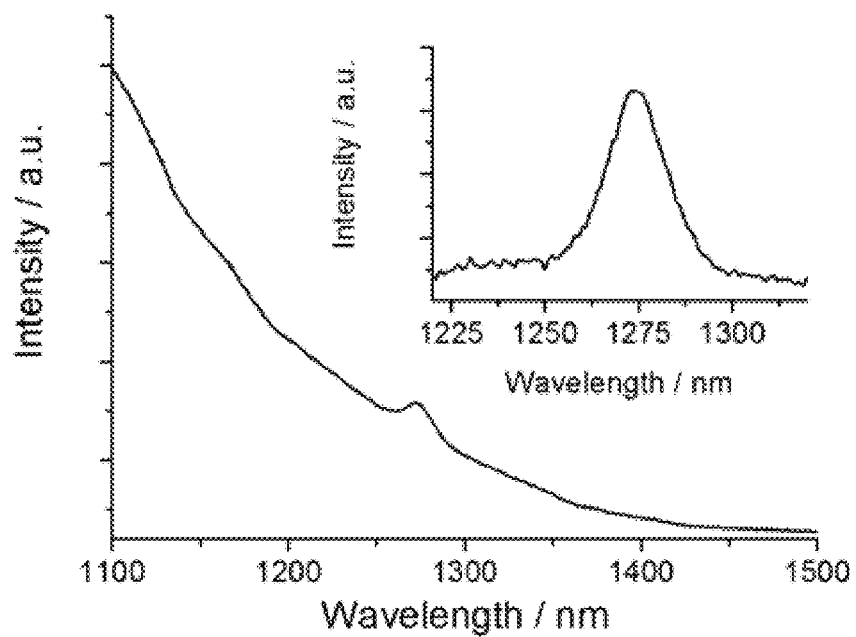

FIG. 11b represents NIR emission spectrum obtained with the $P_1C$ covered blue LED with corrected spectrum in inset.

Figure 12:
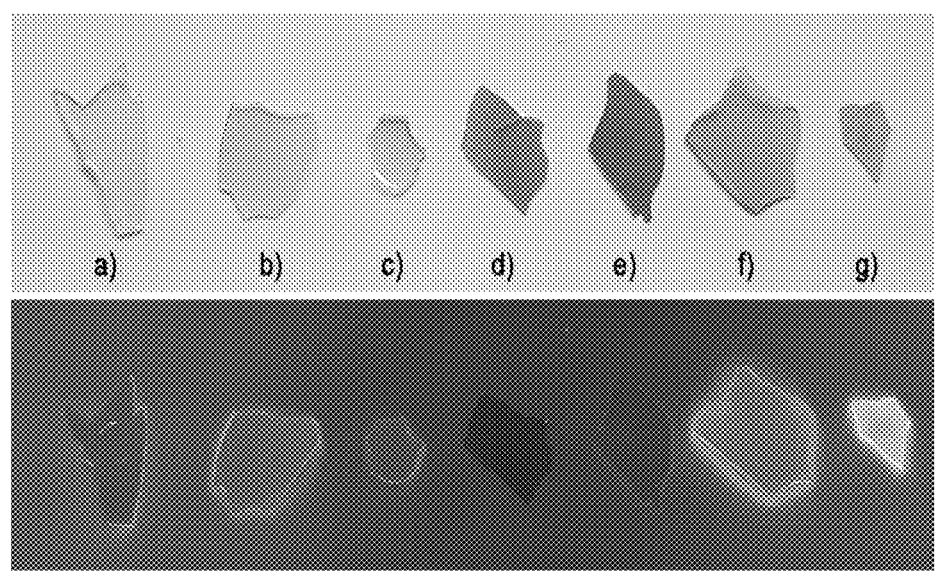

FIG. 12 represents pieces of P2 (PEOMA-PMMA) copolymer doped with a) $Cs_2Mo_6Cl_{14}$ b) $Cs_2Mo_6Br_8Cl_6$ c) $Cs_2Mo_6Br_{14}$ d) $Cs_2Mo_6Br_8I_6$ e) $Cs_2Mo_6I_{14}$ f) $Cs_2Mo_6I_8$ $(OCOC_3F_7)_6$, g) $Cs_2W_6I_{14}$ metal cluster salts under white light (top) and UV light (bottom).

Figure 13:
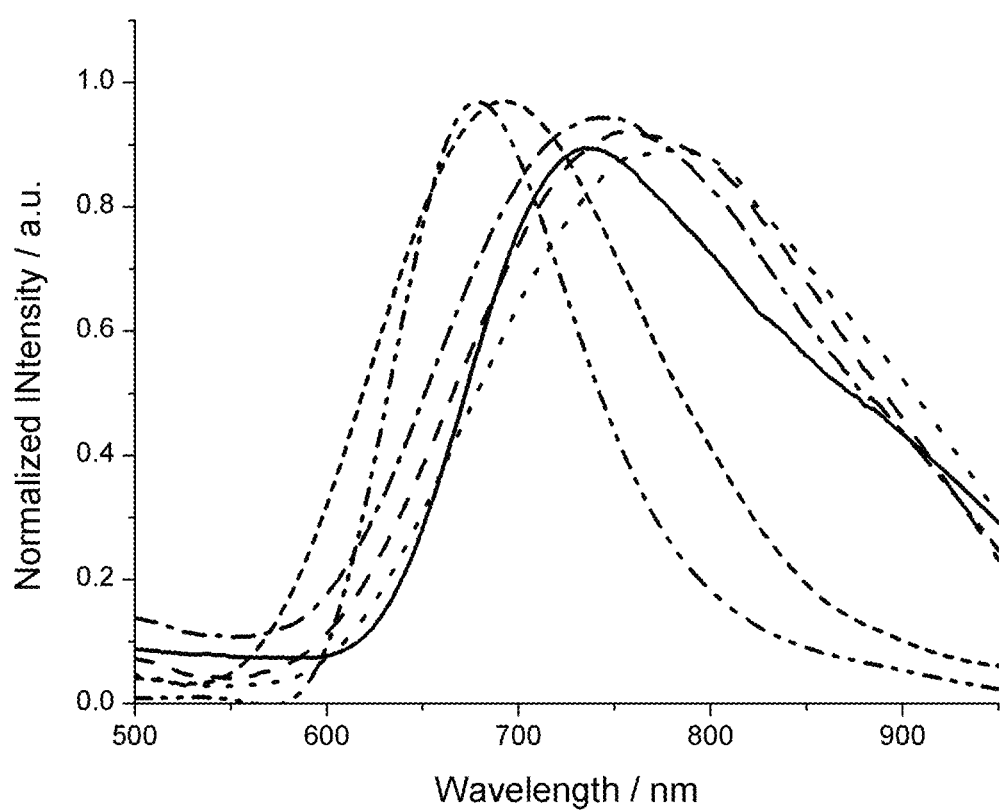

FIG. 13 displays the emission spectra of P2 samples doped at 5 wt % with $Cs_2Mo_6I_{14}$ (plain line), $Cs_2Mo_6Cl_{14}$ (dashed line), $Cs_2Mo_6Br_8I_6$ (dotted line), $Cs_2Mo_6Br_8Cl_6$ (dashed-dotted line), $Cs_2Mo_6I_8(OCOC_3F_7)_6$ (dashed-dotted-dotted line) or $Cs_2W_6I_{14}$ (short-dashed line).

Figure 14:
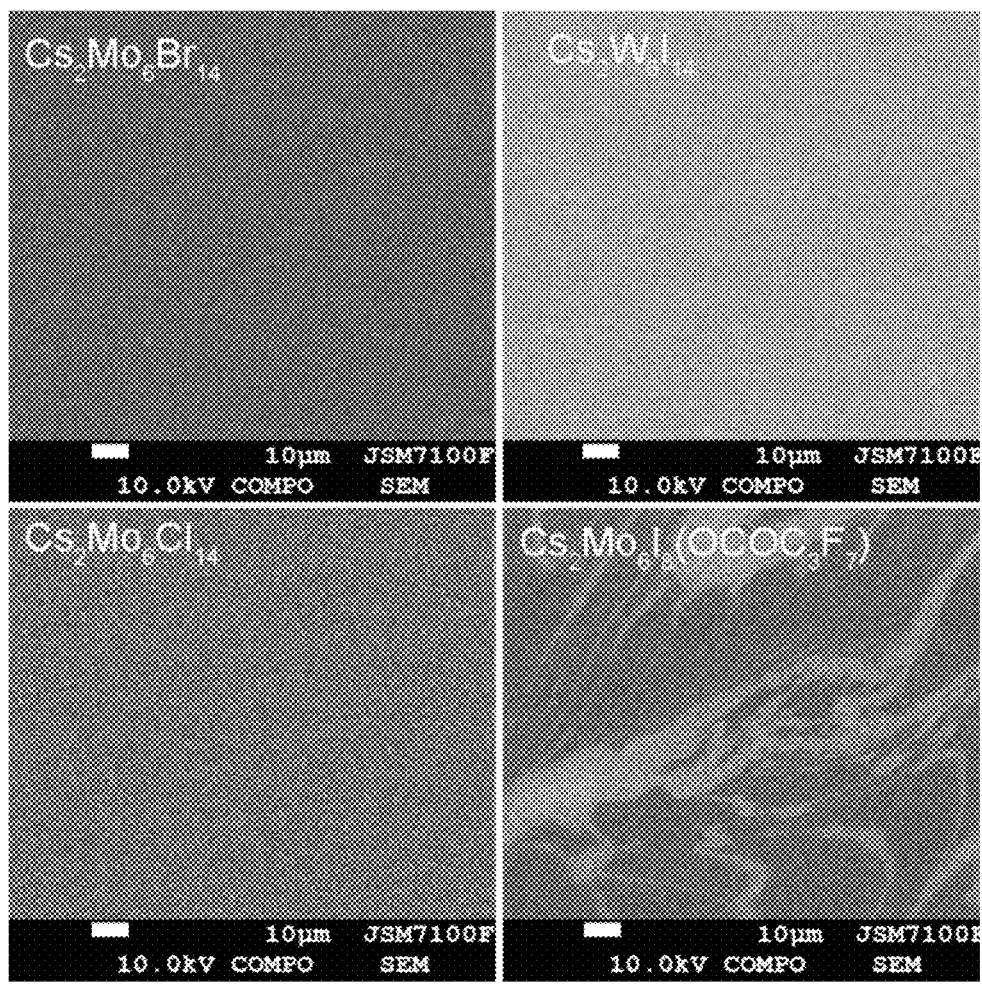

FIG. 14 represents SEM pictures of P2 samples doped with 5 wt % of $Cs_2Mo_6Br_{14}$, $Cs_2W_6I_{14}$, $Cs_2Mo_6Cl_{14}$ and $Cs_2Mo_6I_8(OCOC_3F_7)_6$.

Figure 15:
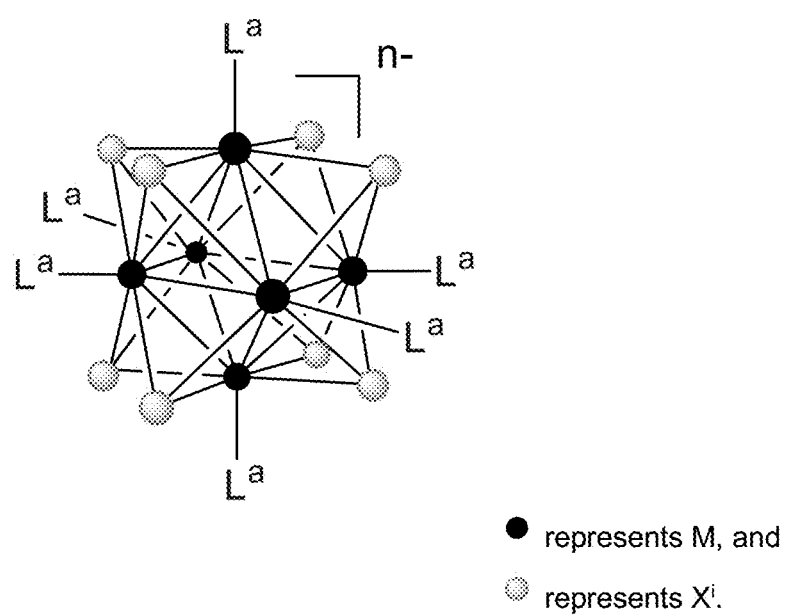

FIG. 15 represents a polyanionic metal nanocluster of general formula $[M_6X^i_8L^a_6]^{n-}$.

Figure 16:
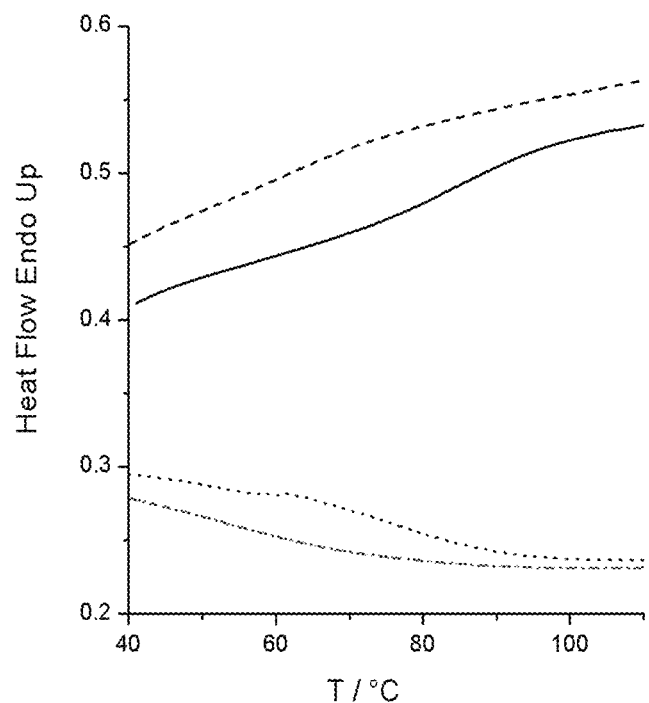

FIG. 16 represents DSC thermograms of PMMA1 on heating (straight) and cooling (dot) and PMMA2 on heating (dash) and cooling (dash-dot) at 10 K·min$^{-1}$.

Figure 17:
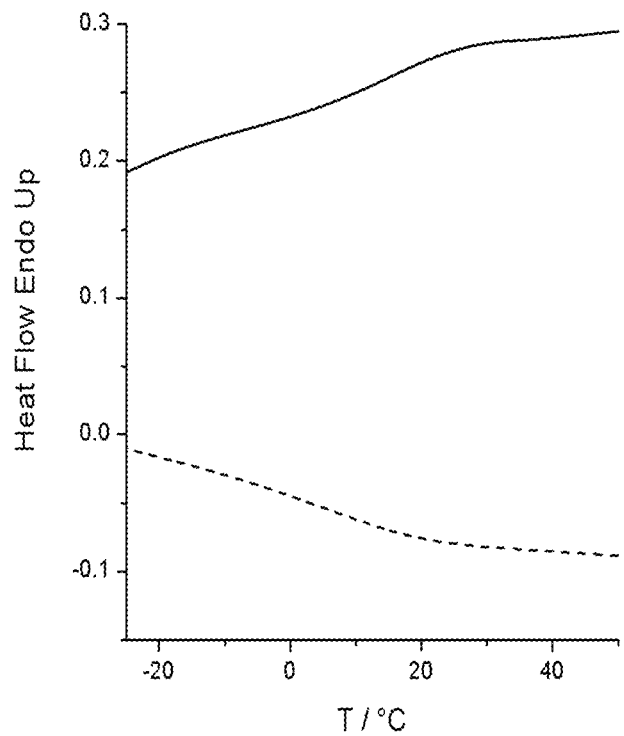

FIG. 17 represents DSC thermograms of PS on heating (straight) and cooling (dash) cycles at 10 K·min$^{-1}$.

Figure 18:
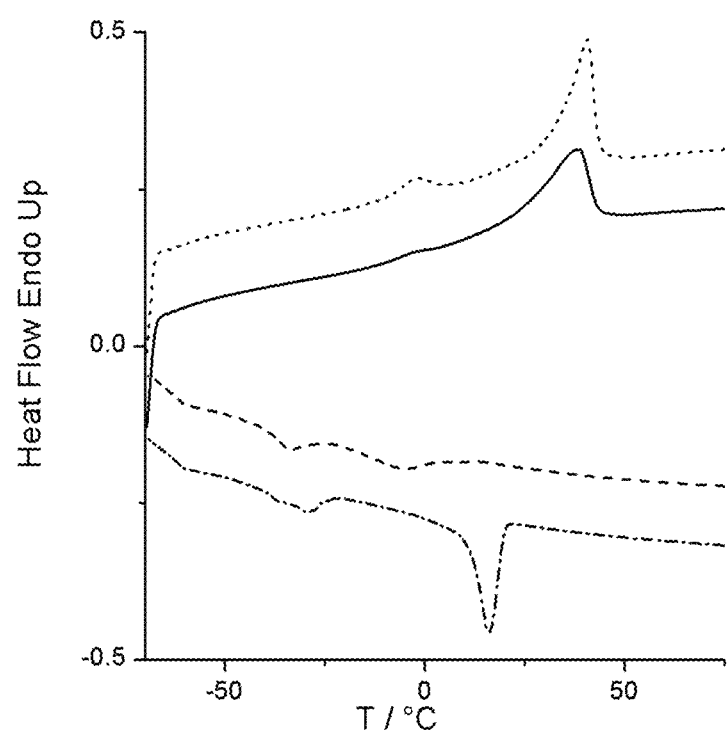

FIG. 18 represents DSC thermograms of PU1 on heating (straight) and cooling (dash) and PU2 on heating (dot) and cooling (dash-dot) at 10 K·min$^{-1}$.

The examples that follow illustrate the invention without limiting its scope in any way.

EXAMPLES

Abbreviations

AIBN: azobisisobutyronitrile
AQY: absolute quantum yield
BD: butandiol
CIE: Commission Internationale d'Eclairage
DBTDL: dibutyltin dilaureate
DSC: differential scanning calorimetry
exc: excitation
FRET: Forster-type resonance energy transfer
FWHM: full width at half maximum
HDI: hexamethylenediisocianate
LED light-emitting diode MAS: magic angle spinning
MMA: methylmethacrylate
NIR: near infrared
NMR: nuclear magnetic resonance
PEO: poly(ethylene oxide)
PEOMA: poly(ethylene oxide) methacrylate
PMMA: polymethylmethacrylate
PS: polystyrene
PU: polyurethane
SEC: size exclusion chromatography
STYPEO: styrene-poly(ethylene oxide)
TEA: triethanolamine
THF: tetrahydrofuran
UV: ultraviolet
wt weight I—Example 1

This first example relates to nanocomposite materials consisting of a polymer-matrix containing polyethyleneglycol grafted with ureasil moieties which are then crosslinked, in which is dispersed the cluster ternary salt $Cs_2Mo_6Br_{14}$.

I-1. Synthesis of the Nanocomposite Materials

O,O'-bis(2-aminopropyl)-poly(ethylene oxide) with a molecular weight of 1900 g·mol$^{-1}$ (Jeffamine® ED-2000), 3-isocyanatopropyltriethoxysilane (ICPTES), ethanol (ETOH) and tetrahydrofuran (THF), were purchased from Sigma-Aldrich. All these chemicals were used as received.

A ureasil-PEO polymer-matrix (PEO1900) was synthesized according to *J. Sol-Gel Sci. Technol.*, 2014, 70:317, by crosslinking of the following polymer in order to form cross-linking ureasil nodes:

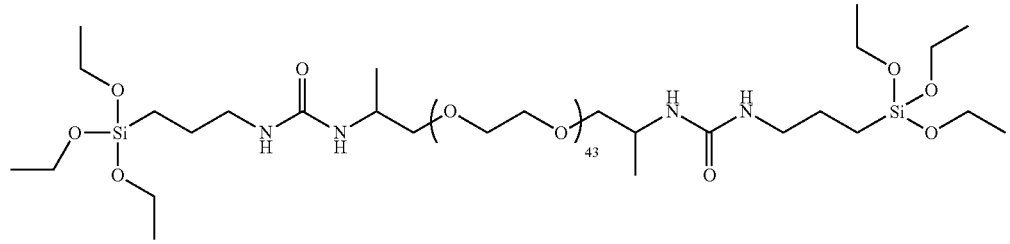

Precursor of PEO 1900

Firstly, the ureasil cross-linking agent was covalently bound to both ends of the macromer polyether by reacting the terminal aminopropyl groups of the end-functionalized PEO. O,O'-bis(2-aminopropyl)-poly(ethylene oxide) (average molecular weight (Mw) 1900 g·mol$^{-1}$) with 3-(isocyanatopropyl)-triethoxysilane in a molar ratio of 1:2 were stirred together in THF under reflux for 24 h at 70° C. The THF solvent was eliminated by evaporation at 60° C., resulting in a hybrid precursor solution. This precursor solution obtained was stored at room temperature in a desiccator to prevent any further hydrolysis reaction. Secondly, silanol moieties were generated and condensation reactions followed to afford cross-linking ureasil nodes. The hydrolysis of —(SiOCH$_2$CH$_3$)$_3$ was initiated by adding 0.035 mL of an aqueous HCl/ETOH solution (2 mol L$^{-1}$) to 1.5 g of precursor which is followed by condensation.

Finally, cylindrical monolithic xerogels of approximately 20 mm diameter and 3 mm height were obtained after drying under vacuum at 70° C. for 24 h.

The ternary salt $Cs_2Mo_6Br_{14}$ was prepared according to *Z. Anorg. Ag. Chem.*, 2005, 631, 411.

The nanocomposite materials were prepared according to one of the following procedures.

Procedure 1:

The ternary salt $Cs_2Mo_6Br_{14}$ was added at different concentrations, namely 0.1, 0.5, 1.0 and 3.0 wt %, to the reaction medium used to perform the hydrolysis step during the preparation of PEO1900. The obtained nanocomposite materials are named E1, E2, E3 and E4 respectively.

Procedure 2:

The ternary salt $Cs_2Mo_6Br_4$ was solubilized in a $H_2O$/EtOH (1:1 v/v) solution at 200 mg·$^{-1}$. The PEO1900 xerogel (0.25 g) obtained as disclosed previously was let to stand in the solution during 24 hours. The cluster adsorption was followed by UV-visible spectrometry (conducted on an Agilent Technologies Cary 60) by monitoring the decrease of the cluster adsorption bands within the mother liquor. The obtained nanocomposite material is named PEO1900CA.

I-2. µX-Ray Fluorescence Spectrometry

The homogeneity of the repartition of the cluster in the polymer-matrix was assessed by µx-ray fluorescence spectrometry for Si, Cs, Mo and Br elements.

Figure 1:
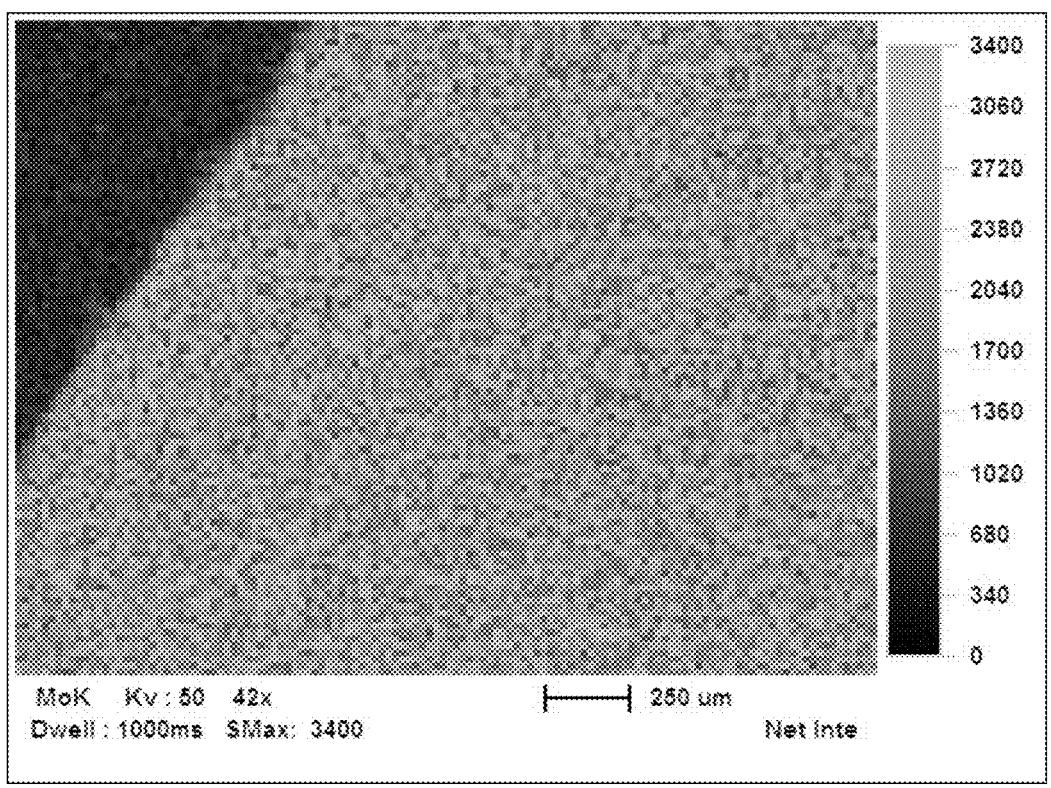
FIG. 1 represents a picture of the nanocomposite E1 obtained by μ X-ray fluorescence spectrometry for Mo element.

FIG. 1 reports results obtained for E1, which assess about the excellent distribution of clusters within the polymer-matrix. Indeed, the homogeneity of colors is an excellent indication of the good repartition of clusters.

I-3. Emission Properties

Material and Methods:

Luminescence spectra were recorded with an ocean optic QE65000 photodetector mounted via an optical fiber on an optical microscope Nikon 80i equipped with a Nikon Intensilight irradiation source. In order to take into account the nonlinear sensitivity of the set up, it was calibrated with an Ocean Optics HL-2000-CAL Calibrated Tungsten Halogen Light Source. Optical filters were used to select the excitation wavelength with a bandwidth of 350-380 nm. Absolute quantum yield measurements were calculated with a Hamamatsu H9920-03G set up.

Figure 2:
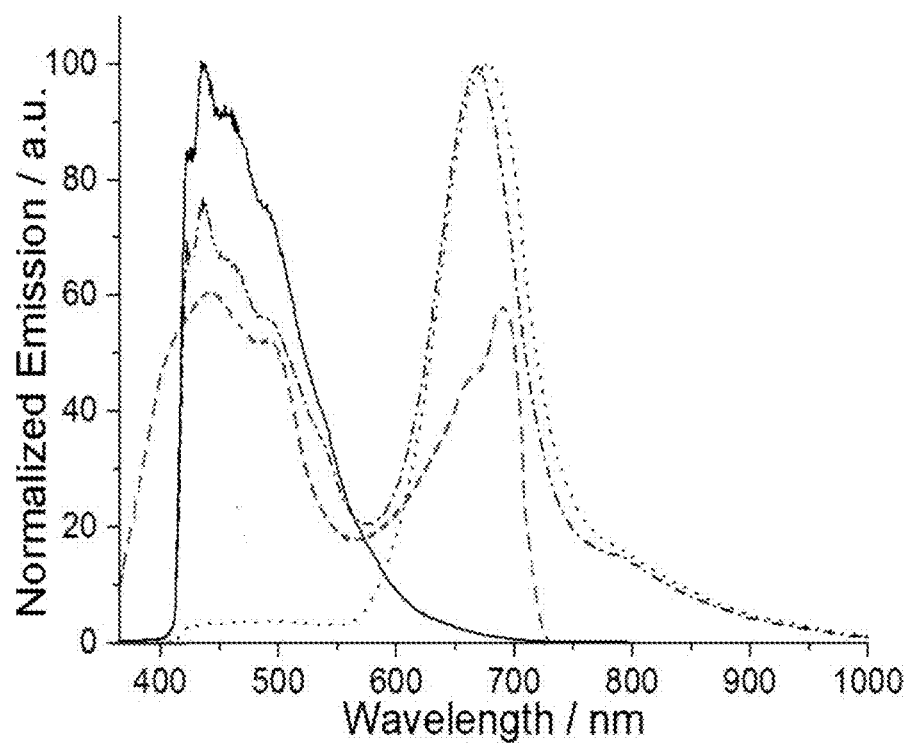
FIG. 2 represents the emission spectra of PEO1900 (black plain line), E2 (black dot-dashed line) and E4 (black dotted line) under 380-400 nm excitation. The photosynthesis active spectrum (absorption spectrum) is also represented in dashed grey line.

Results:

The obtained emission spectra are presented in FIG. 2.

Exciting samples at 350-380 nm induces a two bands emission. The higher energetic band with a maximum located around 450 nm corresponds to the emission of the ureasil matrix, while the broad signal with a maximum around 680 nm is related to the cluster red-NIR emission.

The proportional decrease of PEO1900 luminescence with the increase of $Cs_2Mo_6Br_{14}$ concentration shows that there is some kind of transfer between both luminophores.

The nanocomposite materials show some gas permeability as the absolute quantum yield (AQY) of cluster emission increases under $N_2$ atmosphere, as demonstrated by values shown in Table 1 below for E4 and PEO1900CA, obtained with $\lambda_{exc}$=380 nm.

TABLE 1

| sample | Air | $N_2$ |
|---|---|---|
| E4 | 0.063 | 0.172 |
| PEO1900CA | 0.076 | 0.171 |

Figure 3:
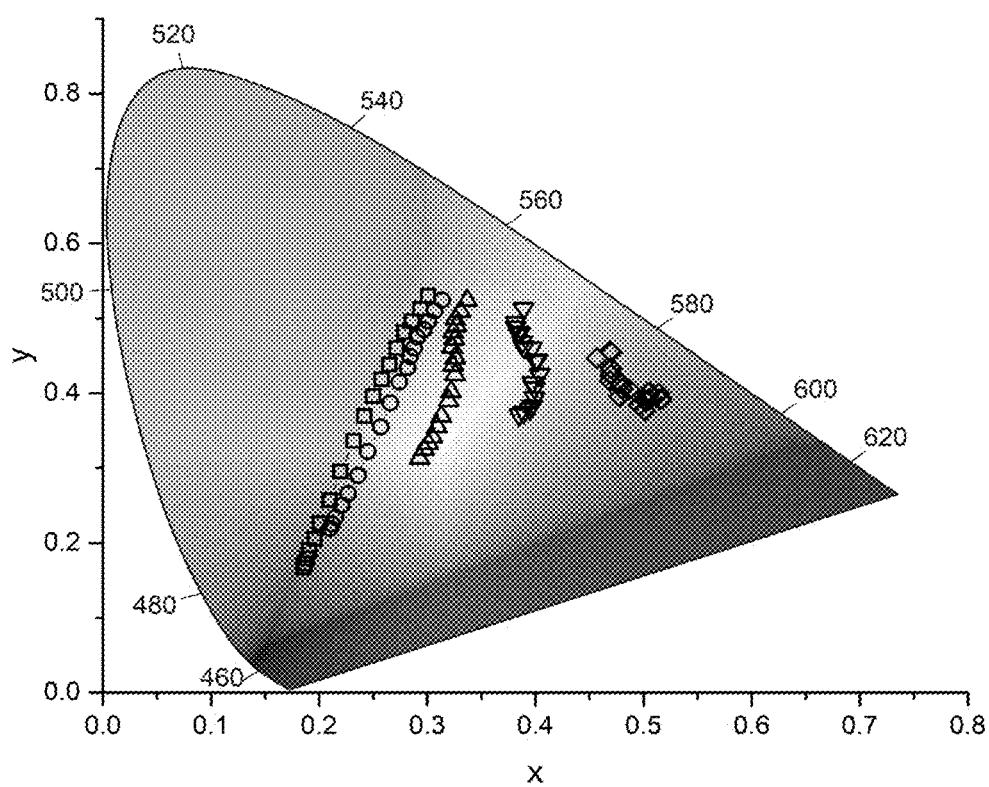
FIG. 3 represents the Commission Internationale d'Eclairage (CIE) 1931 Chromaticity diagram for PEO1900 (reference, square) and nanocomposite materials E1 (circle), E2 (triangle), E3 (inverted triangle) and E4 (diamond) according to the invention as a function of the excitation wavelength (from 365 nm up to 450 nm, every 5 nm).

FIG. 3 plots the CIE 1931 xy chromaticity diagrams for all samples as a function of the excitation wavelength. The CIE chromaticity diagram is a color space designed to represent all the colors perceived by a human eye [Evans, Douglas, *Anal. Chem.*, 2006, 78, 5645; Hunt, *Measuring Colour*, Ellis Horwood, Chichester 1991]. Color-matching functions, related to the response of the cones in a human eye, are used to represent the profile of a given emission spectrum as a set of (x, y) color coordinates on the CIE chromaticity diagram. It seems straightforward that for E2 sample white luminescence is achieved for excitation wavelength varying from 365 up to 385 nm.

Moreover, it shows that by varying the doping concentration and the excitation wavelength, the emission can be tuned across the entire visible spectrum.

I-4. Synthesis of Other Nanocomposite Materials

Using procedure 2 of example 1, several metal cluster salts, namely $Cs_2Mo_6Cl_{14}$, $Cs_2Mo_6Br_8Cl_6$, $Cs_2Mo_6Br_8I_6$, $Cs_2Mo_6I_{14}$, $Cs_2Mo_6I_8(OCOC_3F_7)_6$, $Cs_2W_6I_{14}$, $(NH_4)_2Mo_6Br_8SCN_6$, $K_2Mo_6Cl_{14}$, $(H_3O)_2Mo_6Cl_{14}$ and $(H_3O)_2W_6Cl_{14}$ were introduced in the PEO xerogel.

The ternary salts $Cs_2Mo_6Cl_{14}$, $Cs_2Mo_6Br_8Cl_6$, $Cs_2Mo_6Br_8I_6$, $Cs_2Mo_6I_{14}$ were prepared according to Prévôt et al. *J. Mater. Chem. C* 2015, 3, 5152.

The ternary salt $Cs_2Mo_6I_8(OCOC_3F_7)_6$ was prepared according to Prévôt et al. *Adv. Funct. Mater.* 2015, 25, 4966-4975.

The ternary salt $Cs_2Mo_6I_8(OCOC_2F_5)_6$ was prepared according to the procedure described in (Dalton Trans., 2016, 45, 237).

The ternary salt $Cs_2W_6I_{14}$ was prepared according to Hummel et al. *Eur. J. Inorg. Chem.* 2016, 5063-5067.

The ternary salt $(NH_4)_2Mo_6Br_8SCN_6$ was prepared by solubilizing $Cs_2Mo_6Br_{14}$ in a water/ethanol (1/1) solution containing an excess of $NH_4SCN$. After stirring at 25° C. for 17 h. the compound was extracted with chloroform and obtained after solvent evaporation.

The ternary salt $K_2Mo_6Cl_{14}$ was prepared according to Lindler et al., Z. Anorg. Allg. Chem., 1923, 130, 209-228

The ternary salt $(H_3O)_2Mo_6Cl_{14}$ was prepared according to Sheldon et al., J. Chem. Soc., 1960, 1007-1014

The ternary salt $(H_3O)_2W_6Cl_{14}$ was prepared according to Schafer et al., Monatsh. Chem. 1971, 102, 1293-1304

FIG. 4 shows the emission spectra of several corresponding hybrids.

Table 2 below gathers the absolute quantum yield emission values obtained for doped PEO xerogel under air or $N_2$ atmosphere.

TABLE 2

| | Xerogel | |
|---|---|---|
| | $AQY_{air}$ | $AQY\ N_2$ |
| $Cs_2Mo_6Cl_{14}$ | 15.2 | 17.5 |
| $Cs_2Mo_6Br_{14}$ | 10.6 | 17.1 |
| $Cs_2Mo_6I_{14}$ | 10.8 | 9.7 |
| $Cs_2Mo_6Br_8I_6$ | 4.3 | 6.9 |
| $Cs_2Mo_6Br_8Cl_6$ | 12.8 | 20.6 |
| $Cs_2Mo_6I_8(OCOC_2F_5)_6$ | 3.3 | 22.1 |
| $Cs_2Mo_6I_8(OCOC_3F_7)_6$ | 2.9 | 17.8 |
| $(NH_4)_2Mo_6Br_8SCN_6$ | 6.0 | 31.6 |
| $K_2Mo_6Cl_{14}$ | 5.6 | 17.2 |
| $(H_3O)_2Mo_6Cl_{14}$ | 2.9 | 5.9 |
| $(H_3O)_2W_6Cl_{14}$ | 0.7 | 1.2 |
| $Cs_2W_6I_{14}$ | 26.1 | 23.8 |

II—Example 2

PEO1900 sample is allowed to stand in a solution of acetone containing $Cs_2Mo_6C_{14}$ at 10 mg·ml$^{-1}$ concentration. The solution is left under stirring and little amount of the solution are taken from time to time to control the cluster concentration by UV-Vis spectroscopy. As depicted by FIG. 5, up to 80 wt % of $Cs_2Mo_6Cl_{14}$ can be adsorbed within the PEO1900 matrix.

III—Example 3

This second example relates to nanocomposite materials consisting of a polymer-matrix containing a PMMA-PEOMA copolymer, in which is dispersed the cluster ternary salt $Cs_2Mo_6I_8(OCOC_2F_5)_6$ (FIG. 6b).

III-1. Synthesis of the Nanocomposites

PEOMA (Poly(ethylene glycol) methyl methacrylate, M=950 g·mol$^{-1}$, 20 $OC_2H_4$ units) and MMA monomers were purchased from Alfa Aesar. MMA was distilled before use. PEOMA initiator agent was remove prior to use. AIBN was purified by recrystallization in diethyl ether prior to use. Toluene (98%) solvent was used as received.

Several PMMA-PEOMA copolymers containing 0, 1, 2 or 5 mol % of PEOMA (respectively referenced as P0 (reference), P1, P2 and P5) were prepared according to the following procedure: PEOMA (0, 178, 357, 905 mg (0, 1, 2 and 5 mol %)) and freshly distilled MMA (1.88 g, 2 ml) were dissolved in 20 ml of toluene. The solution was then degassed with argon during 15 min. After addition of 0.2 wt % of AIBN compared to MMA, the solution was heated at 80° C. under argon atmosphere during 24 hours. Purification of the product was achieved by performing at least two precipitations in toluene/methanol solvents. The obtained precipitate was filtered, washed with methanol and dried using a rotavapor. The samples were obtained as white powder after drying under vacuum for 17 h.

The nanocomposite materials, named respectively $P_1C$, $P_2C$ and $P_5C$, were prepared according to the following procedure:

a solution of Pi in acetone was mixed with a solution of acetone containing 10 wt % (compared to the polymer) of $Cs_2Mo_6I_8(OCOC_2F_5)_6$. $P_iC$ samples were obtained after evaporation of the resulting solution.

The $^1$H NMR spectra obtained for $P_0$ and the $P_iC$ samples are detailed below:

$^1$H NMR (400 MHz, CDCl$_3$, δ):

$P_0$: 3.62 (s, 3H, COO—CH3), 2.38 (s, toluene), 2.04-1.73 (m, 2H, CH$_2$), 1.56 (s, HDO), 0.96 (d, J=68.7 Hz, 3H, C—CH3)

$P_1C$: 3.67 (s, 1H, C$_2$H$_4$O—CH$_3$), 3.62 (s, 3H, COO—CH$_3$), 2.38 (s, toluene), 2.04-1.73 (m, 2H, CH$_2$), 1.57 (s, HDO), 0.96 (d, J=68.7 Hz, 3H, C—CH$_3$)

$P_2C$: 3.67 (s, 2H, C$_2$H$_4$O—CH$_3$), 3.62 (s, 3H, COO—CH$_3$), 2.04-1.73 (m, 2H, CH$_2$), 0.96 (d, J=68.7 Hz, 3H, C—CH$_3$)

$P_5C$: 3.67 (s, 3H, C$_2$H$_4$—O—CH$_3$), 3.62 (s, 3H, COO—CH$_3$), 2.04-1.73 (m, 2H, CH$_2$), 1.59 (s, HDO), 0.96 (d, J=68.7 Hz, 3H, C—CH$_3$)

III-2. Organic-Inorganic Interactions

MAS solid state $^{133}$Cs was realized to observe the organic-inorganic moieties interactions (see respectively FIG. 7).

$^{133}$Cs MAS NMR spectra of crystalline Cs$_2$Mo$_6$I$_8$(OCOC$_2$F$_5$)$_6$ contains 2 signals located at −4.97 ppm and −106.52 ppm corresponding to the two crystallographic positions of Cs$^+$ within the Cs$_2$Mo$_6$I$_8$(OCOC$_2$F$_5$)$_6$ crystal structure. When Cs$_2$Mo$_6$I$_8$(OCOC$_2$F$_5$)$_6$ is mixed with pure PMMA, these two signals remain exactly in the same position showing that the metal cluster salt crystalizes within the polymer and does not interact with the polymer matrix.

For P1C, P2C and P5C, only one signal appears at −30.69 ppm, −36.56 ppm, −37.92 ppm, respectively.

The significate shift of Cs$^+$ signal in MAS $^{133}$Cs NMR experiments observed when the ternary salt is integrated in the copolymer matrix assesses the strong interactions existing between the alkali cluster counter cations with the PEO lateral chains.

III-3. Absorption and Emission Properties

Absorption measurements were realized in acetonitrile solution for all samples and show that pure copolymers have a very low absorption after 320 nm (FIG. 8). Thus, doped copolymers absorption spectra contain mainly the cluster absorption bands between 350 and 450 nm, the most suitable UV-blue area to irradiate the ternary salt and observe its strong red-NIR emission.

Doped copolymers were deposited on quartz substrates and irradiated at 370 nm to observe the cluster broad phosphorescence emission band centered around 680 nm (FIG. 9).

Absolute quantum yield (AQY) measurements were realized alternatively in air or N$_2$ atmosphere and show a perfectly reversible enhancement of the AQY from 8% up to around 50% (Table 3). Such change in the emission efficiency is due to the quenching of the cluster excited state by triplet oxygen [a) Jackson et al., J. Phys. Chem., 1990, 94, 4500-4507; b) Jackson et al., Chem. Mater., 1996, 8, 558-564; c) Ghosh et al., Appl. Phys. Lett., 1999, 75, 2885-2887]. This phenomenon being a physical phenomenon, it is perfectly reversible as it does not imply any degradation of the material.

Lifetime of the emissive species were determined using a nanosecond YAG Laser exciting the samples at 355 nm. Obtained results are summarized in the table below. In all cases, the emission decay profile could be fitted with a long component and a short component as previously observed when the same inorganic anion was integrated via ionic assembling in a polyurethane matrix [Amela-Cortes et al., Chem. Commun., 2015, 51, 8177-8180]. Measurements under a N$_2$ flow induce an increase of the longer component from 80 μs to around 200 μs that correlates well with the behavior of phosphorescent dyes dynamically quenched by molecular oxygen [Lu, Chen, Chemical Society Reviews, 2012, 41, 3594-3623]. Indeed, a 200 μs phosphorescence lifetime fits well to the usual emission lifetime of the ternary salt observed in fully degassed solution [Maverick et al., J. Am. Chem. Soc., 1983, 105, 1878-1882]. Hence, these experiments show that the developed integration method does not affect the abilities of clusters to strongly emit.

TABLE 3

| Sample | PEOMA [Mol %] | Φ N$_2$ | Φ air | τ [μs] Air | τ [μs] N$_2$ |
|---|---|---|---|---|---|
| $P_0$ | — | | | | |
| $P_1C$ | 1.2 | 50 | 8 | 30 (0.53) | 30 (0.20) |
| | | | | 80 (0.47) | 200 (0.80) |
| $P_2C$ | 2 | 51.7 | 12 | 30 (0.59) | 30 (0.24) |
| | | | | 90 (0.41) | 190 (0.76) |
| $P_5C$ | 5 | 50 | 8 | 20 (0.05) | 50 (0.10) |
| | | | | 70 (0.95) | 210 (0.90) |

N.B.: Φ: calculated absolute quantum values under air and N$_2$ atmosphere (accuracy 10%); τ: calculated phosphorescence lifetime decay (contribution in parenthesis) for clusters doped copolymers.

Following the procedure described in Robin et al., ACS Appl. Mater. Interfaces, 2015, 7, 21975-21984 for inkjet printing of a blend of Cs$_2$Mo$_6$I$_8$(OCOC$_2$F$_5$)$_6$ cluster precursor (5 wt %) and an epoxy based ink (SU8 2000.5), $P_1C$ copolymer has been inkjet printed on glass substrates. FIGS. 10a and 10b shows inkjet printed thin film and drops under UV light excitation ($\lambda_{exc}$=370 nm).

Contrary to previously printed SU8 thin film that contained half amount of clusters, $P_1C$ printed film shows no phase segregation leading to a good local homogeneity.

This observation highlights the important contribution of the PEO chains in the design and stability of the hybrid.

Thus, high AQY combined with high doping level with no phase segregation makes this copolymer an excellent candidate for optical applications.

III-4. Coated LED

The red emitting doped copolymers have been combined with a UV-blue commercial LED to demonstrate their potentialities in display or lighting applications.

To do so, a thin film of $P_1C$ was deposited by drop casting on top of a commercially available 395 nm UV-blue LED.

The emission spectra were recorded for the LED with and without copolymer coating and with different viewing angles (FIG. 11a). The native UV-blue LED emission spectrum possesses two components, the most intense centered at 395 nm and its corresponding second harmonic at 790 nm.

Once coated with $P_1C$, the emission spectra depend significantly on the orientation of the optical fiber used to record the signal compared to the normal of the LED plan. At 0°, the radiative energy transfer from blue to red is only partial because the copolymer layer is not thick enough to absorb all the UV light. As a result, the blue component of the emission is stronger than the red one. When the angle increases, the red emission becomes stronger compared to the blue LED emission. This phenomenon is mainly due i) to the fact that increasing the angle of detection implies that the UV light passes through an increased polymer thickness and thus more clusters are excited, and ii) to the ability of polymers to guide the emitted light.

This example shows the high potential of this red phosphorescent copolymer as external conversion layer for optical applications.

Moreover, as demonstrated above with AQY measurements under air or inert atmosphere, the cluster triplet excited state reacts efficiently with triplet oxygen to generate the emissive singlet oxygen and, compared to pure doped PMMA [Amela-Cortes et al. *Dalton Trans.*, 2016, 45, 237-245], the introduction of PEO chains strongly affects the hybrids gas permeability.

We therefore investigated whether it was possible to detect directly singlet oxygen emission when the hybrid polymer was deposited as a thin film either on a quartz substrate or irradiated by the blue LED. As shown in FIG. 11b, irradiating the nanocomposite at 375 nm leads to the appearance of a weak emission band centered around 1270 nm related to singlet oxygen emission.

Therefore, a simple device made of a UV-LED covered with our copolymer could act as a local $^1O$ generator, of particular interest for photodynamic therapy like in dermatology for e.g. melanoma treatments [Hong-Tao, Yoshio, *Science and Technology of Advanced Materials*, 2014, 15, 014205], or bactericidal photodynamic applications [Beltran et al., *J. Mater. Chem. B*, 2016, 4, 5975-5979.].

IV—Example 4

Previous P2 (PEOMA-PMMA) copolymer (200 mg) was dissolved in acetone. 10 mg of metal cluster salt (5 wt % compared to P2 amount) were dissolved in acetone. Metal cluster salt used were: $Cs_2Mo_6Cl_{14}$, $Cs_2Mo_6Br_8Cl_6$, $Cs_2Mo_6Br_{14}$, $Cs_2Mo_6Br_8I_6$, $Cs_2Mo_6I_{14}$, $Cs_2Mo_6I_8(OCOC_3F_7)_6$, $Cs_2W_6I_{14}$, $Cs_2Mo_6I_8(OCOC_2F_5)_6$, $(NH_4)_2Mo_6Br_8SCN_6$ and $K_2Mo_6Cl_{14}$. Both solutions were mixed and stirred for 10 minutes. Homogeneous films of doped polymers were obtained by slow evaporation. FIG. 12 represents pieces of polymers under white light and UV light containing different metal cluster salts a) $Cs_2Mo_6Cl_{14}$ b) $Cs_2Mo_6Br_8Cl_6$ c) $Cs_2Mo_6Br_{14}$ d) $Cs_2Mo_6Br_8I_6$ e) $Cs_2Mo_6I_{14}$ f) $Cs_2Mo_6I_8(OCOC_3F_7)_6$, g) $CS_2W_6I_{14}$. The doped copolymers emission spectra are presented in FIG. 13. The homogeneity of films was further confirmed by SEM-EDAX analysis as depicted by FIG. 14 for different samples highlighting that no phase segregation is observed (no spots corresponding to a high metal concentration observed).

Table 4 below gathers the absolute quantum yield emission values obtained for doped copolymers under air or $N_2$ atmosphere.

TABLE 4

|  | P2 | |
| --- | --- | --- |
|  | $AQY_{air}$ | $AQY\ N_2$ |
| $Cs_2Mo_6Cl_{14}$ | 12.1 | 13.7 |
| $Cs_2Mo_6Br_{14}$ | 11.3 | 13.5 |
| $Cs_2Mo_6I_{14}$ | 8.9 | 11.4 |
| $Cs_2Mo_6Br_8I_6$ | 4.2 | 4.5 |
| $Cs_2Mo_6Br_8Cl_6$ | 14.1 | 16.4 |
| $Cs_2Mo_6I_8(OCOC_2F_5)_6$ | 8 | 51.7 |
| $Cs_2Mo_6I_8(OCOC_3F_7)_6$ | 14 | 26.6 |
| $(NH_4)_2Mo_6Br_8SCN_6$ | 13.5 | 26.9 |
| $K_2Mo_6Cl_{14}$ | 8.9 | 15.9 |
| $Cs_2W_6I_{14}$ | 22.2 | 26.5 |

V—Example 5

This example relates to nanocomposite materials consisting of a polymer-matrix containing either a PMMA-PEO, a PS-PEO or a PU-PEO copolymer, in which is dispersed the cluster ternary salt $Cs_2Mo_6I_8(OCOC_2F_5)_6$. In the PMMA-PEO and the PU-PEO copolymers, the PEO chains are located on the main chain of the copolymer, while in the PS-PEO copolymer, the PEO chains are grafted onto the backbone PS chain as side-chains.

V-1. Synthesis of the Nanocomposite Materials

Reagents:
MMA monomer was purchased from Alfa Aesar. MMA was distilled before use. AIBN was purified by recrystallization in diethyl ether prior to use. PEO-bisamine (CAS 24991-53-5), PEO-diacrylate (CAS 26570-48-9), and PS-PEO (see formula below) were purchased from Specific Polymers and used without further purification. Butandiol, hexamethylenediisocianate, dibutyltin dilaureate, triethanolamine were purchased from Sigma Aldrich and used without further purification.

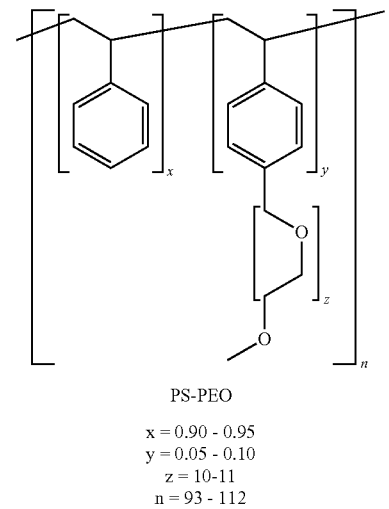

PS-PEO x = 0.90 - 0.95
y = 0.05 - 0.10
z = 10-11
n = 93 - 112

Synthesis of the Nanocomposite Materials
Comprising a PMMA-PEO Matrix

Procedure 1:
$Cs_2Mo_6I_8(OCOC_2F_5)_6$ cluster compound was dissolved in 4 mL of dry THF and mixed to PEO-diacrylate (at 1 wt %). The mixture was heated at 50° C. under stirring to homogenized and the solvent was evaporated. The mixture PEO-diacrylate/$Cs_2Mo_6I_8(OCOC_2F_5)_6$ was added to distilled MMA (at 20 wt %). The mixture was homogenized in an ultrasounds bath for 5 min. Radical initiator AIBN (0.2 wt %) was added and the mixture was subjected to ultrasounds for 5 min. The solution was kept for 72 h in an oven at 70° C. A transparent light-yellow solid nanocomposite material was obtained, which is named PMMA1.

Procedure 2:
$Cs_2Mo_6I_8(OCOC_2F_5)_6$ cluster compound was mixed with PEO-diacrylate (at 10 wt %) and to that, distilled MMA was added (20 wt % PEO-diacrylate/Mo to MMA). The mixture was homogenized in an ultrasounds bath for 5 min. Radical initiator AIBN (0.2 wt %) was added and the mixture was homogenized in an ultrasounds bath for 5 min. The mixture was then kept at 70° C. in an oven for 72 h. A dark orange solid nanocomposite material was obtained, which is named PMMA2.

Table 5 below shows glass transition temperatures (Tg) measured by differential scanning calorimetry 10K/min of two samples ($2^{nd}$ cooling cycle) (see also FIG. 16).

TABLE 5

| Sample | Cluster in PEO (wt %) | Cluster total (wt %) | MMA (mg) | PEO (mg) | Cluster (mg) | $T_g$ (° C.) |
|---|---|---|---|---|---|---|
| PMMA1 | 1 | 0.2 | 800 | 200 | 2 | 81.3 |
| PMMA2 | 10 | 2 | 800 | 200 | 20 | 61.3 |

Synthesis of the Nanocomposite Material Comprising a PS-PEO Matrix

PS-PEO was dissolved in 4 mL of dry THF and to that $Cs_2Mo_6I_8(OCOC_2F_5)_6$ cluster compound was added (1 wt % of total mass). The mixture was homogenized by stirring at 50° C. and the solvent evaporated. A transparent orange solid nanocomposite material was obtained, which is named PS.

Table 6 below shows glass transition temperature (Tg) measured by differential scanning calorimetry 10K/min of the samples ($2^{nd}$ cooling cycle) (see also FIG. 17).

TABLE 6

| Sample | Cluster total (wt %) | PS-PEO (mg) | STYPEO (wt %) | Cluster (mg) | $T_g$ (° C.) |
|---|---|---|---|---|---|
| PS | 1 | 990 | 5-10 | 10 | 11.5 |

Synthesis of the Nanocomposite Materials Comprising a PU-PEO Matrix

Procedure 1:

$Cs_2Mo_6I_8(OCOC_2F_5)_6$ cluster compound was dissolved in 4 mL of dry THF and mixed to PEO-bisamine matrix (at 1 wt %). The mixture was heated at 50° C. under stirring to homogenized and the solvent was evaporated. The mixture PEO-bisamine/$Cs_2Mo_6I_8(OCOC_2F_5)_6$ (23 wt % total mass) and butandiol (BD, 11.5 wt %) was heated to 80° C. to melt to afford a homogeneous mixture. To that, hexamethylene-diisocianate (HDI, 60 wt %), the catalyst dibutyltin dilaureate (DBTDL, 1 mL) and the crosslinker triethanolamine (TEA, 2.9 wt %) were added. The mixture was kept for 72 h at 70° C. to afford a light orange segmented elastomer. The obtained nanocomposite material is named PU1.

Procedure 2:

$Cs_2Mo_6I_8(OCOC_2F_5)_6$ cluster compound) was mixed to PEO-bisamine matrix (at 10 wt %) by heating to 80° C. for 5 min (23% wt of PEO-bisamine to total mass). Once the mixture wax homogeneous butandiol (BD, 11.5 wt %) was added. To that, hexamethylenediisocianate (HDI, 60 wt %), the catalyst dibutyltin laureate (DBTL, 1 mL) and the crosslinker triethanolamine (TEA, 2.9 wt %) were added. The mixture was kept for 72 h at 70° C. to afford a dark orange segmented elastomer. The obtained nanocomposite material is named PU2.

Table 7 below shows the composition of two materials as well as the $T_g$ and the melting temperatures (Tm), determined by DSC at a rate of 10 K/min of two samples ($2^{nd}$ cooling cycle) (see also FIG. 1).

TABLE 7

| Sample | Cluster in PEO (wt %) | Cluster total (wt %) | BD (mg) | HDI (mg) | PEO (mg) | TEA (mg) | $T_g$ (° C.) | $T_{m1}$ (° C.) | $T_{m2}$ (° C.) |
|---|---|---|---|---|---|---|---|---|---|
| PU1 | 1 | 0.23 | 100 | 525 | 200 | 25 | −61.9 | −36.9 | −8.5 |
| PU2 | 10 | 2.3 | 360 | 672 | 200 | 25 | −62 | −38 | 21 |

V-2. Optical Properties

The following table 8 gathers the optical data of the previous nanocomposite materials.

TABLE 8

| Sample | $I_{max}$ | FWHM ($cm^{-1}$) | AQY excitation 365 nm under air | AQY after 3 min under N2 flow |
|---|---|---|---|---|
| PMMA1 | 700 | 2313 | 2.0 | 3.1 |
| PS | 700 | 2452 | 1.1 | 2.5 |
| PU1 | 700 | 2449 | 2.8 | 3.4 |
| PU2 | 690 | 2366 | 10.7 | 19.0 |
| PMMA2 | 678 | 2492 | 3.0 | 5.0 |

The invention claimed is:

1. A solid nanocomposite material consisting of a polymer-matrix in which are dispersed alkali metal, hydronium or ammonium salts of polyanionic metal clusters,
   wherein the alkali metal, hydronium or ammonium salts of the polyanionic metal clusters are salts or a mixture of salts of the general formula $A_nM_6X^i{}_8L^a{}_6$, wherein:
   A represents Cs, Na, K, a hydronium or $NR_1R_2R_3R_4$, wherein $R_1$ to $R_4$ represent, independently of each other, a hydrogen atom or a $C_1$-$C_6$ alkyl group;
   n ranges from 2 to 5;
   M represents Mo, W, Re or a mixture thereof;
   $X^i$ is an inner ligand and represents a halogen atom or a mixture thereof; and
   $L^a$ is an apical ligand and represents a halogen atom, an organic ligand or a mixture thereof,
   wherein the polymer-matrix comprises at least a linear or branched polymer or copolymer containing one or several poly(ethylene oxide) (PEO) chains, said polymer or copolymer being optionally crosslinked and each PEO chain having at least 4 ethylene oxide monomer units, and
   wherein the salts of polyanionic metal clusters interact with the polymer-matrix solely by means of weak interactions in between the alkali metal, hydronium or ammonium cation and the PEO chains of polymer or copolymer.

2. The nanocomposite material according to claim 1, wherein:
   $X^i$ represents Cl, Br, I or a mixture thereof; and
   $L^a$ represents Cl, Br, I, CN, SCN, a carboxylate or a mixture thereof.

3. The nanocomposite material according to claim 1, wherein the alkali metal, hydronium or ammonium salts of the polyanionic metal clusters are selected from the group consisting of $Cs_2Mo_6Br_{14}$, $Cs_2Mo_6Cl_{14}$, $Cs_2Mo_6I_{14}$, $Cs_2Mo_6Br_8C_{16}$, $Cs_2Mo_6Br_8I_6$, $Cs_2Mo_6I_8(OCOC_2F_5)_6$, $Cs_2Mo_6I_8(OCOC_3F_7)_6$, $(NH_4)_2Mo_6Br_8SCN_6$, $K_2Mo_6Cl_{14}$, $Cs_2W_6I_{14}$, $(H_3O)_2Mo_6Cl_{14}$, $(H_3O)_2W_6Cl_{14}$ and mixtures thereof.

4. The nanocomposite material according to claim 1, wherein the polymer or copolymer is:
   at least a linear PEO polymer,
   at least a branched copolymer containing PEO chains grafted as side-chains onto the backbone chain of the copolymer, or
   at least a linear or branched copolymer containing one or several PEO chains that are part of the backbone chain of the copolymer.

5. The nanocomposite material according to claim 1, wherein the polymer-matrix comprises at least a linear PEO polymer, optionally with one or two identical or different light-emitting moieties grafted on its extremities.

6. The nanocomposite material according to claim 1, wherein the polymer or copolymer is selected from the group consisting of PEO, crosslinked PEO-ureasil, crosslinked PEO-urethanesil, polymethylmethacrylate-poly(ethylene oxide) methacrylate (PMMA-PEOMA), polydimethylsiloxane-PEO (PDMS-PEO), polyvinylpyrrolidone-PEO (PVP-PEO), polyurethane-PEO (PU-PEO), polystyrene-PEO (PS-PEO), polyethylene-PEO (PE-PEO) polyester-PEO (PES-PEO), polyamide-PEO, polycaprolactone-PEO and mixtures thereof.

7. A photonic device comprising a nanocomposite material according to claim 1.

8. The photonic device according to claim 7, wherein it is a light-emitting diode (LED) coated with a film of the nanocomposite material.

9. A method for crop growth comprising lighting a crop with the photonic device according to claim 7.

10. A method for emitting phosphorescence comprising irradiating the nanocomposite material according to claim 1 with a light having a wavelength in the range comprised between 340 nm and 480 nm.

11. A method for generating singlet oxygen comprising reacting the nanocomposite material according to claim 1 with triplet oxygen.

12. A process for preparing a nanocomposite material according to claim 1, comprising a step:
   of dipping the polymer-matrix in a solution containing the dissolved alkali metal, hydronium or ammonium salts of the polyanionic metal clusters, or
   of polymerizing the monomer units of the polymer or copolymer as defined in claim 1 in a reaction medium containing the alkali metal, hydronium or ammonium salts of the polyanionic metal clusters, or
   of crosslinking a polymer or copolymer precursor in order to obtained a crosslinked polymer or copolymer as defined in claim 1 in a reaction medium containing the alkali metal, hydronium or ammonium salts of the polyanionic metal clusters.

13. A solid nanocomposite material consisting of a polymer-matrix in which are dispersed alkali metal, hydronium or ammonium salts of polyanionic metal clusters, wherein the alkali metal, hydronium or ammonium salts of the polyanionic metal clusters are salts or a mixture of salts of the general formula $A_nM_6X^i_8L^a_6$, wherein:
   A represents Cs, Na, K, a hydronium or $NR_1R_2R_3R_4$, wherein $R_1$ to $R_4$ represent, independently of each other, a hydrogen atom or a $C_1$-$C_6$ alkyl group;
   n ranges from 2 to 5;
   M represents Mo, W or a mixture thereof;
   $X^i$ is an inner ligand and represents a halogen or a chalcogen atom or a mixture thereof; and
   $L^a$ is an apical ligand and represents a halogen atom, an organic ligand or a mixture thereof,
wherein the polymer-matrix comprises at least a linear or branched polymer or copolymer containing one or several poly(ethylene oxide) (PEO) chains, said polymer or copolymer being optionally crosslinked and each PEO chain having at least 4 ethylene oxide monomer units, and
wherein the salts of polyanionic metal clusters interact with the polymer-matrix solely by means of weak interactions in between the alkali metal, hydronium or ammonium cation and the PEO chains of polymer or copolymer.

14. The nanocomposite material according to claim 13, wherein:
   $X^i$ represents Cl, Br, I or a mixture thereof; and
   $L^a$ represents Cl, Br, I, CN, SCN, a carboxylate or a mixture thereof.

15. The nanocomposite material according to claim 13, wherein the polymer or copolymer is:
   at least a linear PEO polymer,
   at least a branched copolymer containing PEO chains grafted as side-chains onto the backbone chain of the copolymer, or
   at least a linear or branched copolymer containing one or several PEO chains that are part of the backbone chain of the copolymer.

16. The nanocomposite material according to claim 13, wherein the polymer-matrix comprises at least a linear PEO polymer, optionally with one or two identical or different light-emitting moieties grafted on its extremities.

17. The nanocomposite material according to claim 13, wherein said polymer or copolymer is selected from the group consisting of PEO, crosslinked PEO-ureasil, crosslinked PEO-urethanesil, polymethylmethacrylate-poly(ethylene oxide) methacrylate (PMMA-PEOMA), polydimethylsiloxane-PEO (PDMS-PEO), polyvinylpyrrolidone-PEO (PVP-PEO), polyurethane-PEO (PU-PEO), polystyrene-PEO (PS-PEO), polyethylene-PEO (PE-PEO) polyester-PEO (PES-PEO), polyamide-PEO, polycaprolactone-PEO and mixtures thereof.

18. A process for preparing a nanocomposite material according to claim 13, comprising a step:
   of dipping the polymer-matrix in a solution containing the dissolved alkali metal, hydronium or ammonium salts of the polyanionic metal clusters, or
   of polymerizing monomer units of the polymer or copolymer as defined in claim 13 in a reaction medium containing the alkali metal, hydronium or ammonium salts of the polyanionic metal clusters, or
   of crosslinking a polymer or copolymer precursor in order to obtain a crosslinked polymer or copolymer as defined in claim 13 in a reaction medium containing the alkali metal, hydronium or ammonium salts of the polyanionic metal clusters.

19. A photonic device comprising a nanocomposite material according to claim 13.

20. The photonic device according to claim 19, wherein it is a light-emitting diode (LED) coated with a film of the nanocomposite material.

21. A method for crop growth comprising lighting a crop with the photonic device according to claim 19.

22. A method for emitting phosphorescence comprising irradiating the nanocomposite material according to claim 13 with a light having a wavelength in the range comprised between 340 nm and 480 nm.

23. A method for generating singlet oxygen comprising reacting the nanocomposite material according to claim 13 with triplet oxygen.

\* \* \* \* \*